United States Patent
Paul et al.

(10) Patent No.: US 8,818,058 B2
(45) Date of Patent: Aug. 26, 2014

(54) METHOD FOR DETERMINING A CORRECTION FUNCTION FOR CORRECTING COMPUTED TOMOGRAPHIC NUMBERS OF A SMALL TARGET OBJECT IN A CT IMAGE

(75) Inventors: Narinder S. Paul, Toronto (CA); Ali Ursani, Toronto (CA); Joerg Blobel, Zoetermeer (NL)

(73) Assignees: Toshiba Medical Systems Corporation, Otawara-shi (JP); University Health Network, Toronto (CA)

( * ) Notice: Subject to any disclaimer, the term of this patent is extended or adjusted under 35 U.S.C. 154(b) by 407 days.

(21) Appl. No.: 12/955,170

(22) Filed: Nov. 29, 2010

(65) Prior Publication Data
US 2011/0129057 A1 Jun. 2, 2011

Related U.S. Application Data

(60) Provisional application No. 61/264,899, filed on Nov. 30, 2009.

(51) Int. Cl.
*G06K 9/00* (2006.01)
(52) U.S. Cl.
USPC ........... 382/128; 382/129; 382/130; 382/131; 382/132; 382/100

(58) Field of Classification Search
None
See application file for complete search history.

(56) References Cited

U.S. PATENT DOCUMENTS

| | | | |
|---|---|---|---|
| 5,615,279 A * | 3/1997 | Yoshioka et al. | 382/131 |
| 7,238,947 B2 * | 7/2007 | Oumi et al. | 250/370.08 |
| 7,471,759 B2 * | 12/2008 | Rinkel et al. | 378/7 |
| 2010/0183213 A1* | 7/2010 | Keppel et al. | 382/131 |

OTHER PUBLICATIONS

Kemerink et al ("The CT's sample volume as an approximate, instrumental measure for density resolution in densitometry of the lung", Med. Phys. 1997).*

Liu et al ("Scale based scatter correction for computer aided polyp detection in CT colonography", Nov. 18, 2008).*

* cited by examiner

*Primary Examiner* — Avinash J Yentrapati
(74) *Attorney, Agent, or Firm* — Oblon, Spivak, McClelland, Maier & Neustadt, L.L.P.

(57) ABSTRACT

A method of correcting target region in computed tomographic (CT) image, including the steps of obtaining a CT image of a patient; determining the size of a target object in the CT image; and correcting CT numbers of a portion of the CT image that corresponds to the target object, based on the determined size of the target object.

14 Claims, 18 Drawing Sheets

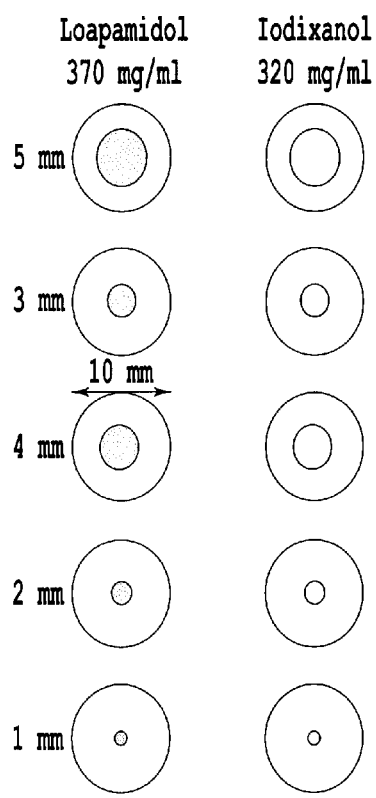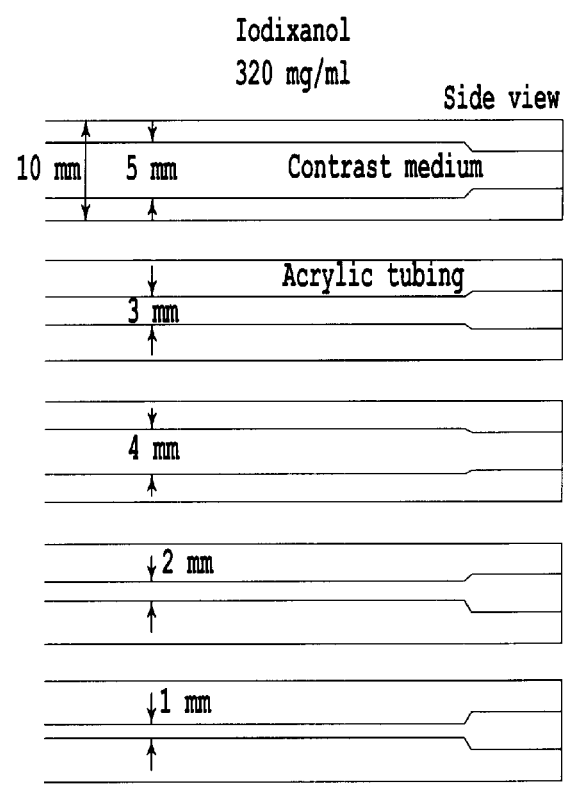
*Fig.3(a)*　　　*Fig.3(b)*

Reconstructed cross sectional CT images of the CV phantom demonstrating ROI placement within the vessel lumen, within the backround medium (m) and on the vessel wall (w).

METHOD FOR DETERMINING A CORRECTION FUNCTION FOR CORRECTING COMPUTED TOMOGRAPHIC NUMBERS OF A SMALL TARGET OBJECT IN A CT IMAGE

CROSS-REFERENCE TO RELATED APPLICATIONS

The present application is related to and claims priority to provisional patent Application No. 61/264,899, filed Nov. 30, 2009, the entire contents of which are incorporated herein by reference.

FIELD

Embodiments described herein generally relate to a method of determining a correction function for correcting computed tomographic (CT) numbers of a target object in a CT image obtained using a given CT scanner, based on a geometric size of the target object, and a method of correcting the target object in the CT image using the correction function.

BACKGROUND

Computed tomography angiography (CTA) is used to exclude significant atherosclerosis in the coronary arteries, cerebrovascular and peripheral vascular systems. Sequential improvements in computed tomography (CT) architecture and software have facilitated significant improvements in the diagnostic accuracy of CTA. For example, for CT coronary angiography (CTCA) these developments include an increased number of detector rows from 64 to 320, faster gantry rotation speeds (≤350 ms), robust ECG gating techniques, automatic optimal phase detecting software and arrhythmia rejection programs. The resultant improvements in temporal and contrast resolution have enabled routine evaluation of the coronary arterial tree down to vessel segments as small as 1.5 mm in diameter and the demonstration of minimal plaque size down to 0.5 mm in diameter. These technical advances have facilitated a high negative predictive value for CTCA in excluding significant arterial disease, based on clear visualization of a vessel segment normal in caliber, without evidence of intimal plaque causing a flow limiting lesion and containing a uniform high signal (HU) from the contrast enhanced lumen. Successful and comprehensive diagnostic CTA requires accurate measurement of vessel caliber down to vessel segments as small as 1 mm, and accurate measurement of the density of contrast media in these small caliber vessels. However, the recent improvements in CT technology have not resulted in improved spatial resolution. This is an important limitation in the detection and accurate characterization of arterial plaque particularly in the coronary arteries. In the U.S., more than 1 million people per annum present with a sudden cardiac event, the majority having no cardiac related symptoms beforehand. A significant number of these patients have "high risk" coronary plaque that is vulnerable to rupture and cause acute coronary artery occlusion. This plaque is multifocal, contains a large, predominantly lipid core, a thin fibrous cap and does not cause significant reduction in the cross sectional area of the vessel lumen prior to rupture. Patients in whom this high risk plaque is detected have a greater than 5% one year risk of acute coronary syndrome or sudden cardiac death. Therefore, accurate measurement of plaque composition is required both for risk stratification and for assessment of strategies that target amelioration or reversal of atherosclerosis. However, the current clinical gold standard for assessment of coronary arterial plaque is intravascular ultrasound (IVUS), an invasive and time consuming technique. Computed tomography is non-invasive, but current CT units use matrix reconstruction algorithms which lead to a reduction in contrast and CT number for smaller objects (vessels and intimal plaque).

BRIEF DESCRIPTION OF THE DRAWINGS

A more complete appreciation of embodiments described herein and many of the attendant advantages thereof will be readily obtained as the same becomes better understood by reference to the following detailed description when considered in connection with the accompanying drawings, wherein:

FIGS. 3A-3C illustrate construction of the CV phantom with an acrylic container housing five pairs of acrylic vessel tubes 10 mm in external diameter, 1-5 mm in luminal diameter filled with diluted iodinated contrast medium of 320 and 370 mg/ml Iodixanol to achieve a luminal CT density of 460 and 550 HU respectively. The CV phantom is shown in the scan position within the CT gantry;

DETAILED DESCRIPTION

Figure 1:
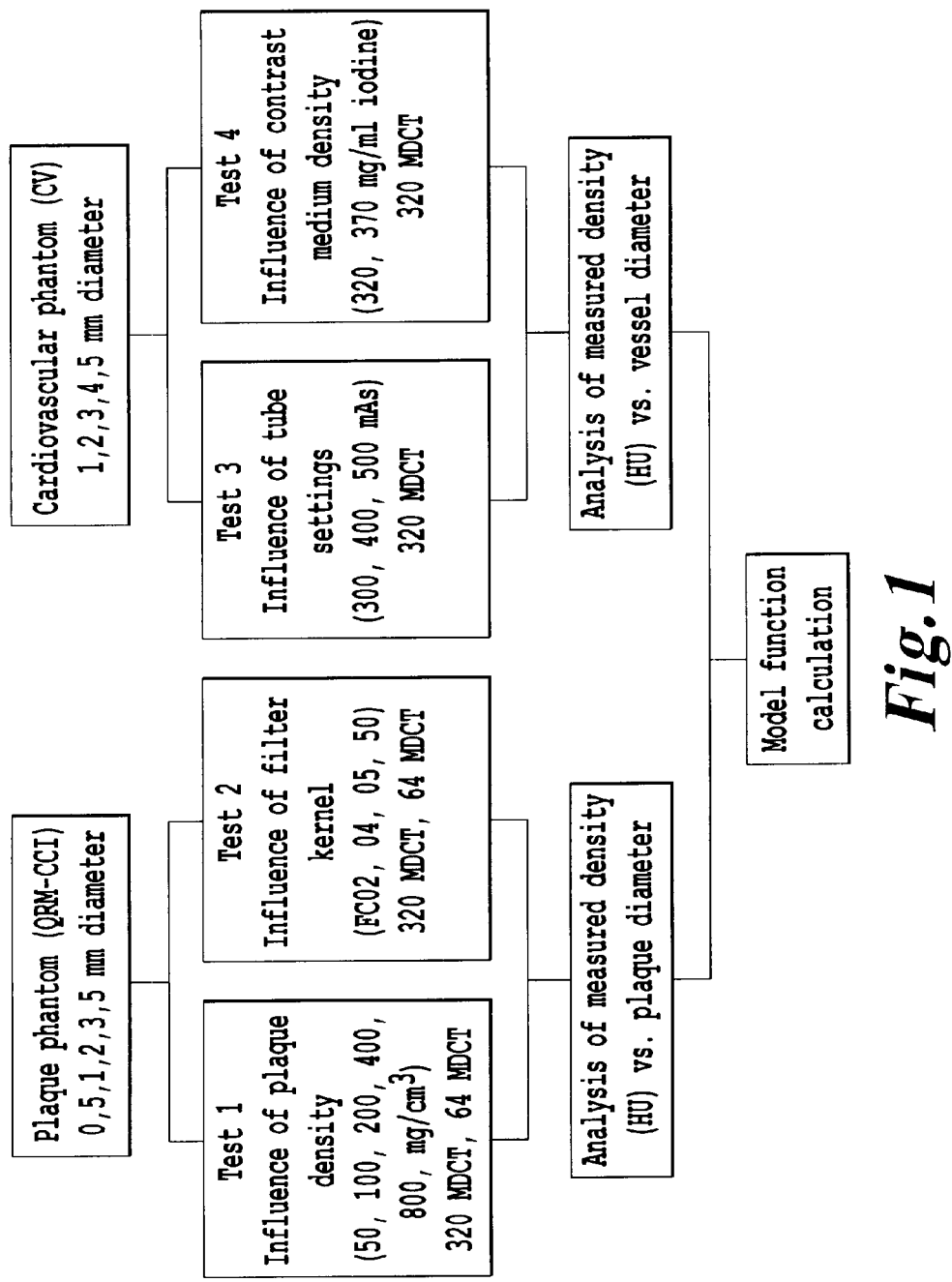
FIG. 1 illustrates a study design to determine the influences of physical plaque density (mg/cm3) and diameter, reconstruction filter kernel, radiation exposure, and contrast media density (mg/ml) and vessel diameter on measured plaque and vessel CT numbers (HU)

Embodiments described herein are directed to a method and system for the accurate determination of coronary vessel and plaque density (HU) for diameters down to 0.5 mm by use of a novel mathematical function that can correct the density-object size relationship.

In one embodiment, a method of correcting a target object in a computed tomographic (CT) image includes the steps of (1) obtaining the target object; (2) determining the size of a target object in the CT image; and (3) correcting CT numbers of a portion of the CT image that corresponds to the target object, based on the determined size of the target object.

In one embodiment, the obtaining step includes (1) performing a CT scan of the patient to obtain projection data; and (2) performing reconstruction to obtain the CT image.

In another embodiment, the determining step includes (1) segmenting the CT image to generate a segmented image; (2) identifying the target object in the segmented image; and (3) measuring the size of the identified target object. The measuring step includes determining an effective radius of the target object or measuring one of a diameter, area, or volume of the target object.

In one embodiment, the correcting step includes correcting each CT number in the CT image that corresponds to the target object using the formula: $N=1-c*\exp(-a*D^b)$, wherein a, b, and c are variables determined from non-linear regression, d is the determined size of the target object, and N is a reduction factor in CT number of the target object. Further, in one embodiment, the correcting step includes multiplying each CT number in the CT image that corresponds to the target object by 1/N.

In still yet another embodiment, the correcting step includes determining a corrected CT image by changing each CT number in the CT image that corresponds to the target object.

In another embodiment, a system for correcting a target object in a computed tomographic (CT) image includes (1) a CT scanner configured to perform a CT scan of a patient to obtain a CT image; and (2) a processor configured to determine a size of the target object in the CT image, and to correct CT numbers of a portion of the CT image that corresponds to the target object, based on the determined size of the target object.

In another embodiment, a method of determining a correction function for correcting computed tomographic (CT) numbers of a target object in a CT image obtained using a CT scanner, based on a geometric size of the target object includes the steps of (1) performing a CT scan of a phantom having a plurality of inserts, each insert having a corresponding known physical density and a corresponding known geometric size, to generate CT image data for the phantom; and (2) performing regression analysis on the CT image data to determine the correction function, the correction function relating attenuation in CT number to geometric size of the target object.

In another embodiment, a system for determining a correction function for correcting computed tomographic (CT) numbers of a target object in a CT image obtained using a CT scanner, based on a geometric size of the target object, includes (1) the CT scanner configured to perform a CT scan of a phantom having a plurality of inserts, each insert having a corresponding known physical density and a corresponding known geometric size, to generate CT image data for the phantom; and (2) a processor configured to perform regression analysis on the CT image data to determine the correction function, the correction function relating attenuation in CT number to geometric size of the target object.

Calcified plaque has been shown to be of prognostic value in predicting the likelihood of future cardiac events. Therefore, coronary artery calcium burden is often assessed using cardiac CT to aid in a patients' cardiac risk stratification. Increasing recognition of the physical characteristics associated with high risk or vulnerable plaque have highlighted the limitations of current CT technology in accurately detecting, characterizing, and determining the physical density [mg/cm3] of non-calcified small volume arterial plaque.

The principle of matrix image reconstruction employed in computed tomography is known to produce a reduction in measured densities of HU values for small objects in CT phantoms and therefore contributes to the difficulty experienced in characterizing vessel plaque with computed tomography. However, the use of a robust and accurate correction factor will compensate for the influence of object size and therefore provide the opportunity for accurately characterizing arterial plaque throughout the arterial system particularly within the coronary arteries or within the internal carotid arteries.

The present inventors have quantified the mathematical relationship that describes the reduction in measured object CT number with object size both for a commercially available plaque phantom and in a purpose-built CV phantom that accurately mimics the CT environment of the epicardial coronary arteries in routine clinical practice. They have determined that the reduction in measured object CT number is independent of plaque actual density, and therefore that the mathematical correction can be applied to calcified and non-calcified (soft) plaque. The decrease in object CT number is also independent of the detector row configuration, contrast medium density, and reconstruction filter kernels routinely used in clinical CTCA. They have also demonstrated that the percentage reduction in object CT number is independent of the applied X-ray tube current. In addition, application of the mathematical correction function will provide accurate plaque quantification and characterization, thereby aiding risk stratification and surveillance for therapies targeted at reversal or inhibition of atherosclerosis.

Though the plaque phantom contained cylindrical shaped objects, in the experiments described herein the CT numbers were compared only with the diameter of the object. This is because in planar CT reconstruction, like axial or curved MPR, the only provision to measuring CT numbers is from diameter or cross-sectional area. In the vessel phantom the contrast media z-length is expanded in comparison with the insert size in plaque phantom. The correction functions for both phantoms are nearly identical. This indicates that the z-dimension has no relevant influence.

EXPERIMENTS

The outline of a set of experiments to determine a relationship between density and object size is shown in FIG. 1. Two phantoms were used to study the relationship between measured CT number and various scan parameters. A commercially available purpose-built phantom (QRM-CCI, QRM GmbH, Moehrendof, Germany) was used for cylindrical shaped objects mimicking plaque of various densities. A second custom-built cardiovascular phantom (CV Phantom) was used to simulate cardiac vessels of varying diameters filled with contrast media of different densities.

Four test sets were designed to examine the individual effect of various plaque densities, filter kernels, X-ray tube settings, and contrast media on the measured CT number in HU. Quantitative analysis was performed using all the measured data to derive a mathematical regression function to define the relationship between measured CT number in HU and the object size represented by the diameter of the object.

Figure 2C:
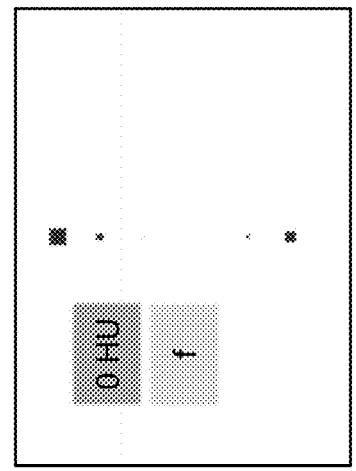
FIGS. 2A-2C illustrate construction of the plaque phantom shown on cross-sectional computed tomography (2a), line diagrams with cross sectional (2b) and long axis views demonstrate the distribution of the five calcium Hydroxyapatite cylinders arranged in five density groups; 50, 100, 200, 400 and 800 mg/cm3 (2b, a-e), and the calibration inserts; one of water equivalent CT density (0 HU) and the other composed of Hydroxyapatite with a density of 186 mg/cm$^3$ (2c, f)
Figure 2B:
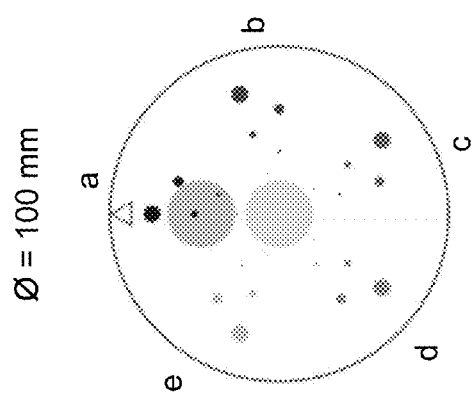
Figure 2A:
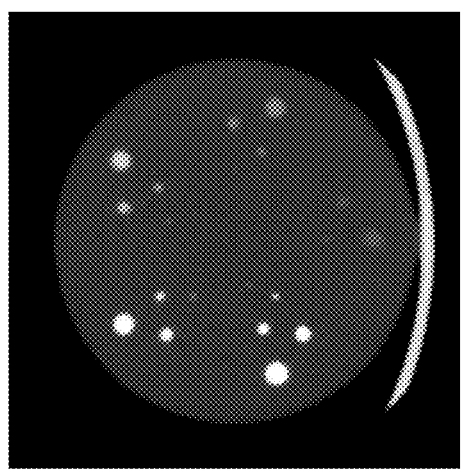

The QRM-CCI plaque phantom shown in FIGS. 2A-2C is designed as a calibration standard for CT number measurements. This phantom is a 100 mm diameter cylindrical object with a background density that mimics soft tissue with an attenuation of 35±5 HU at 120 kVp. Two calibration inserts are provided within the phantom, one with water equivalent attenuation of 0±3 HU @ 80-120 kVp and the second insert is made of Hydroxyapatite (HA) with a known density of 186 $mg/cm^3$. In addition, the plaque phantom contains Calcium Hydroxapatite (CaHA) cylinders in five density groups; 50, 100, 200, 400 and 800 mg/cm3. The cylinders represent 3D plaque objects and measure 0.5, 1, 2, 3, and 5 mm in diameter and length.

Figure 3C:
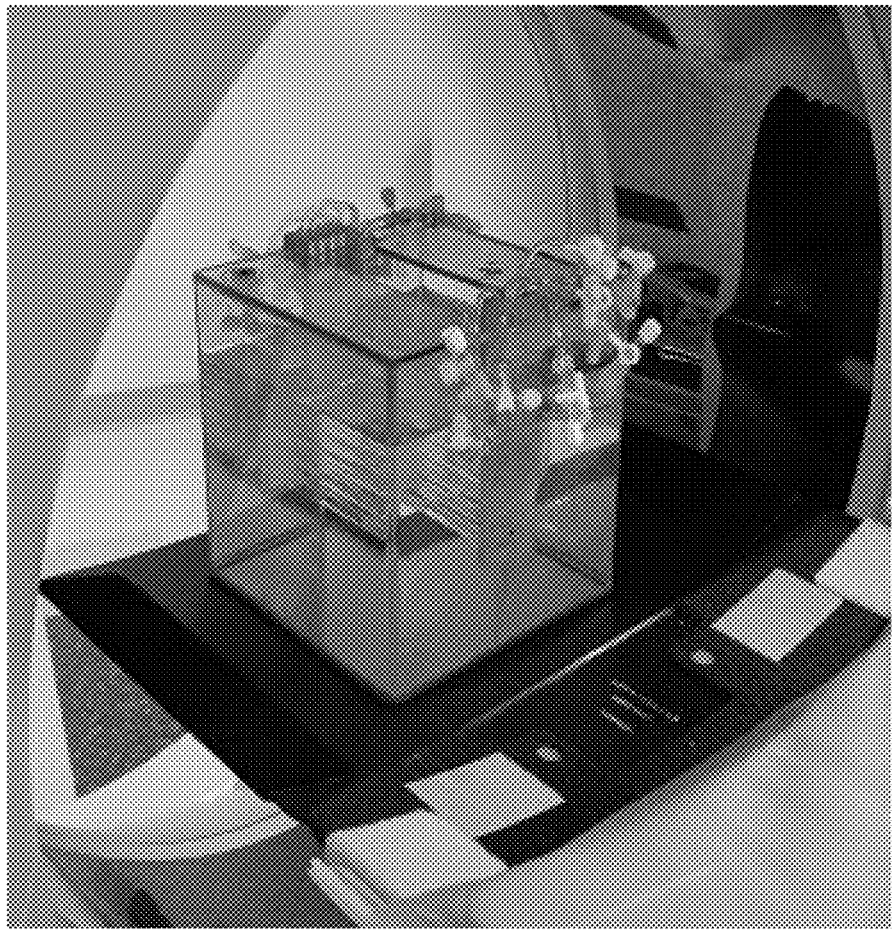
Figure 4:
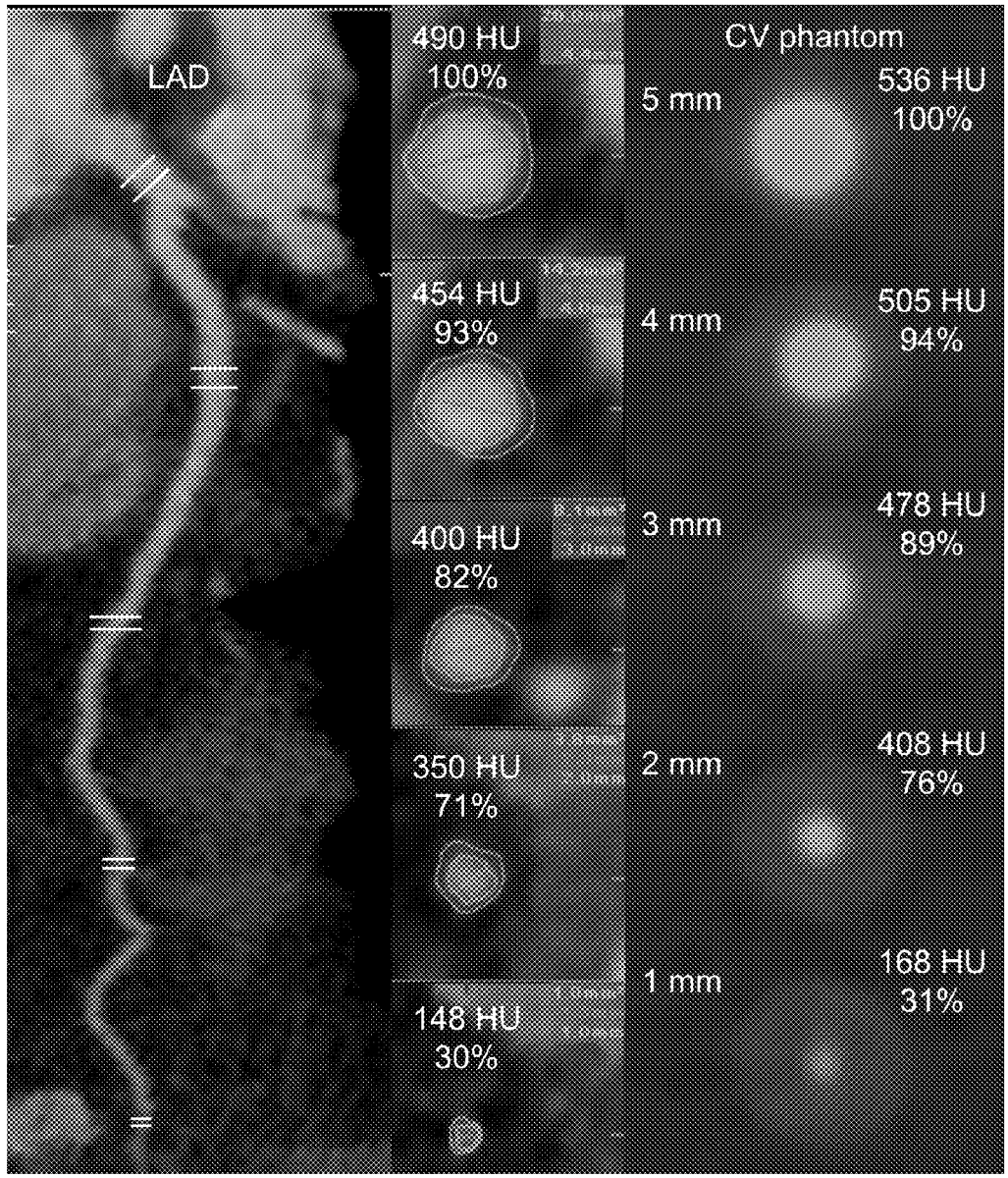
FIG. 4 shows computed tomography images comparing a clinical CT coronary angiogram using (a) a curved multiplanar image and (b) selected axial cross sectional images of a normal left anterior descending coronary artery with (c) cross sectional axial images through the CV phantom demonstrating lumen diameters and contrast CT-number measurements (HU)

The CV Phantom shown in FIGS. 3A-3C was constructed to mimic the relationship between arterial segments and surrounding body tissues on CT angiography (CTA). For the purposes of this study, we attempted to stimulate the relationship between epicardial coronary arteries and the myocardium by analyzing clinical CT coronary angiograms performed on 64 and 320 multi-detector CT (FIG. 4). The CV Phantom consists of a 20×20×20 cm acrylic container, filled with normal saline (0.9% NaCl) and iodinated contrast media (320 mg/ml) titrated to 1:85 ratio in order to achieve a background CT number of 90 HU @ 120 kVp that approximated to the CT number for myocardial density.

The acrylic container contains a detachable insert consisting of two rows of five acrylic tubular "vessels" with internal diameters of 1, 2, 3, 4, and 5 mm to replicate the range of diameters found in adult human coronary arteries. The outer diameter of all the vessel tubes was 10 mm and the measured CT number of the acrylic wall was 130 HU @ 120 kVp. This blended well with the tissue equivalent background solution so that the "vessel wall" was less conspicuous. The vessel tubes were filled with iso-osmolar iodinated contrast media currently used for clinical CT coronary angiography and diluted with normal saline (1:14 ratio) in order to simulate peak arterial (aortic) luminal density in HU. One set of vessel tubes was filled with Iodixanol 320 mg/ml (Visipaque, GE Healthcare, Ontario, Canada) titrated to a luminal CT number of 460 HU, the other set of vessel tubes were filled with Iopamidol 370 mg/ml (Isovue, Bracco, Quebec, Canada), with a resulting luminal CT number of 550 HU.

Three multi-detector CT units were used in this study; a volume CT (320 MDCT) using 320×0.5 mm detectors (AquilionONE™, Toshiba Medical Systems, Tokyo, Japan) and two 64 MDCT (64 MDCT1 and 64 MDCT2) with 64×0.5 mm detector rows (Aquilion64™, Toshiba Medical Systems, Tokyo, Japan). The maximum in-plane resolution for all three CT scanners was 0.35×0.35 $mm^2$.

Both phantoms were scanned on 64 MDCT and 320 MDCT using a tube potential of 120 kVp, 1.5 s gantry rotations, 24 cm FOV and image reconstruction with a section thickness of 0.5 mm with 0.25 mm overlap. The 64 MDCT employed a helical pitch (gantry rotation per table movement) of 0.64; the 320 MDCT used a volume acquisition with z-coverage of 16 cm without table movement.

The initial series of scans involved the plaque phantom and were designed to determine the difference between measured CT number and inherent plaque density values for a spectrum of plaque densities (50, 100, 200, 400 and 800 HU, Test 1) and different reconstruction filter kernels (FC02, FC04, FC05 and FC50, Test 2). For this test, X-ray tube settings of 120 kV and 600 mAs were used. The selected image acquisition parameters ensured a radiation dose threshold value such that the smallest cylinder (0.5 mm in diameter and 0.5 mm in length) with the least lumen CT number (50 HU) was visible on reconstructed CT images. Below this radiation dose threshold, the resultant image noise obscured detection of this cylinder.

The test scans that involved the CV phantom were used to evaluate the variance in luminal contrast density measured in CT number for all vessels (1-5 mm luminal diameter) scanned with three different tube settings (300, 400 and 500 mAs, Test 3) and using 2 different contrast media varying in their iodine content (320 mg/ml and 370 mg/ml, Test 4).

Axial images were reconstructed with 0.5 mm slice thickness, 0.25 mm interval for both phantoms. Additional images with 3 mm slice thickness and 1.5 mm overlap were reconstructed for the plaque phantom to reflect clinical practice for performing coronary artery calcium assessment. Images were reconstructed with overlap in order to reduce partial-volume effects and to increase detection of small diameter lesions. The CT images were processed with four different filter kernels FC02, FC04, FC05, and FC50 that the manufacturer has established for CT coronary angiography. FC02, FC04 use a smooth filter kernel whereas FC05 and FC50 combine a smooth filter kernel with mild edge enhancement.

In order to minimize the influence of viewing conditions and software, the acquired DICOM images were analyzed at three different workstations each with dedicated viewing software; Vitrea2™ (Vital Images, Inc. Minnesota U.S.A.), Fusion PACS, (Merge Technologies Inc. Milwaukee, USA) and propriety CT display consoles supplied with the CT units (Toshiba Medical Systems, Tokyo, Japan).

Figure 5A:
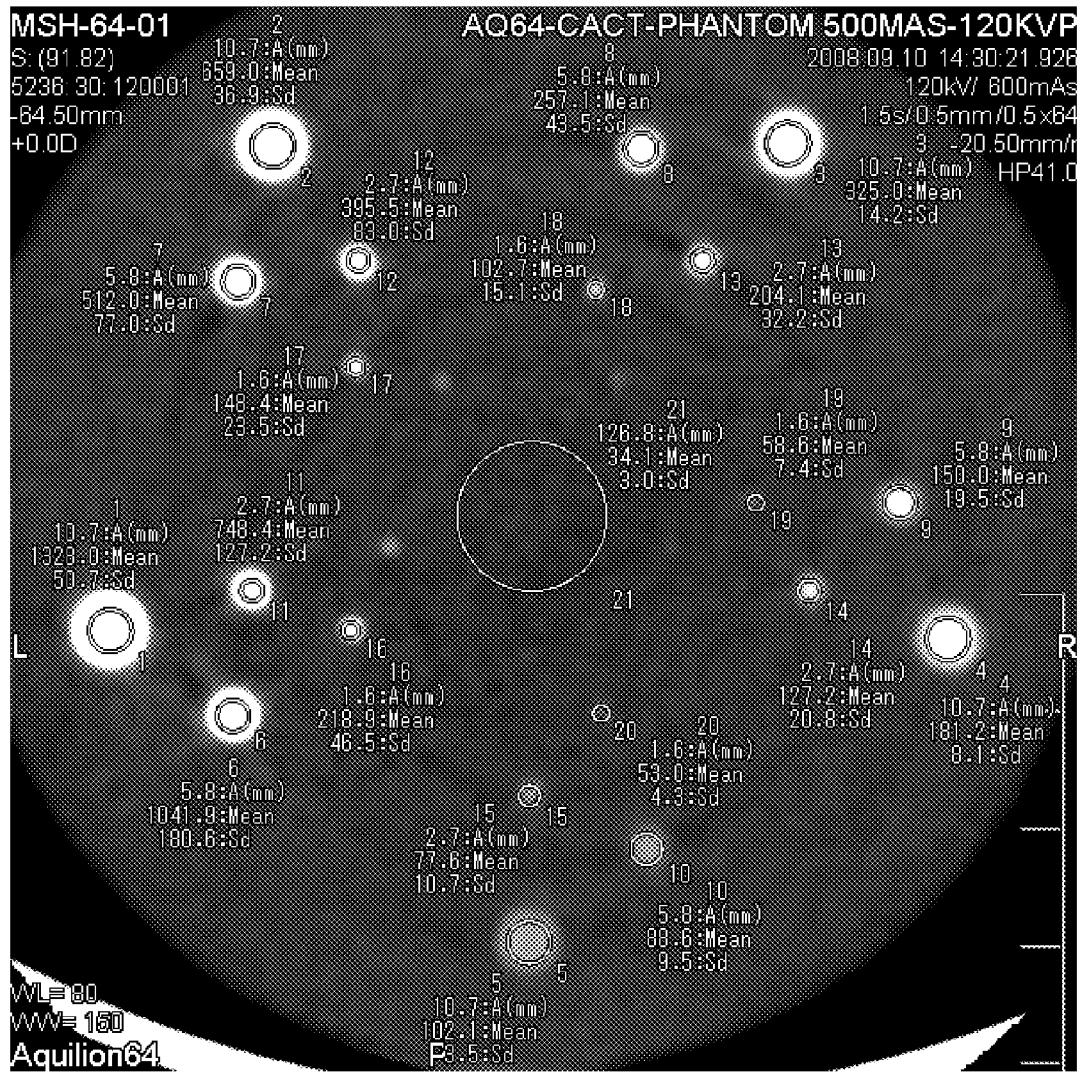
FIGS. 5A and 5B show CT density measurements of the plaque phantom (DPlaque) with regions of interest (ROI) placement on five cylindrical pearls (0.5-5 mm) within each of five density-groups 800 to 50 mg/cm3 (a) and on the water (DWater) and Hydroxyapatite (DHA) calibration cylinders (b)
Figure 5B:
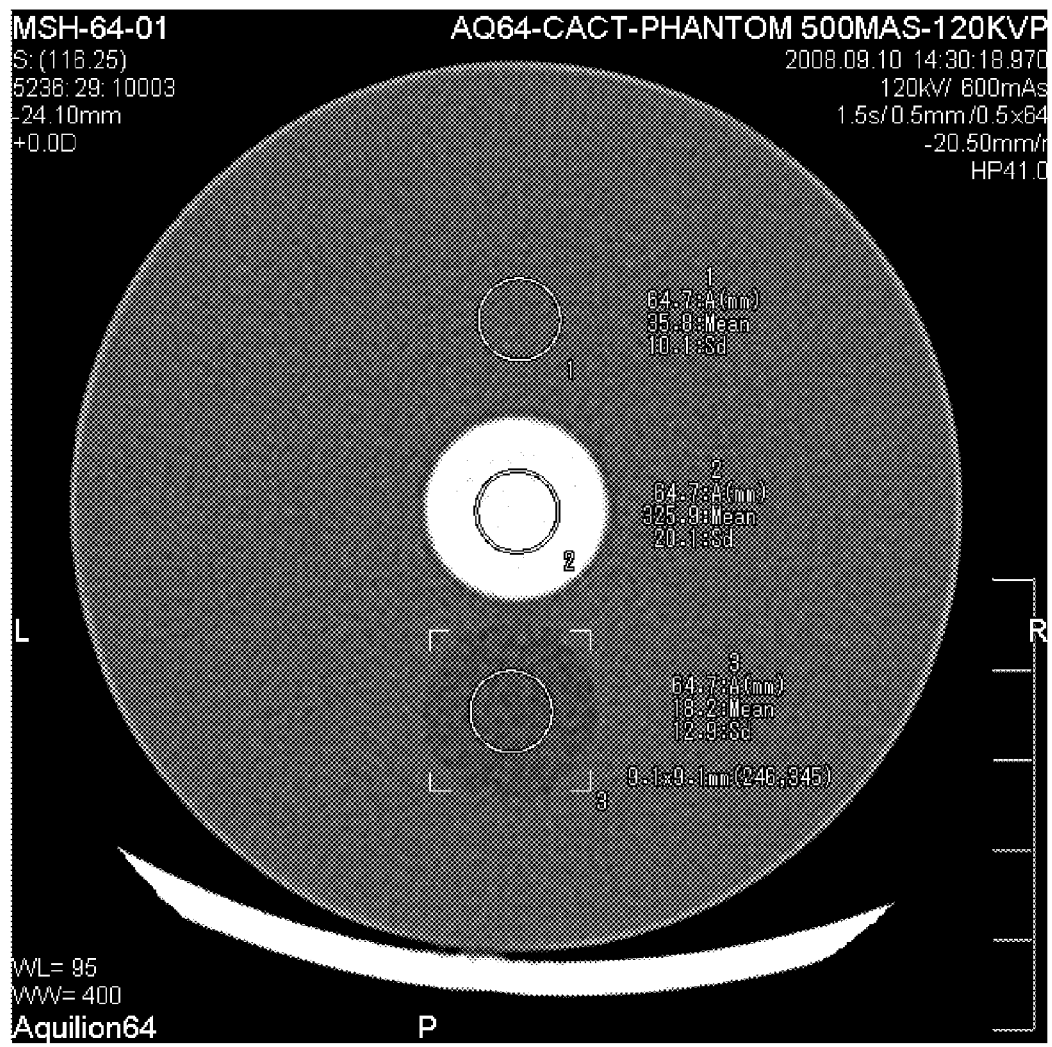
Figure 6:
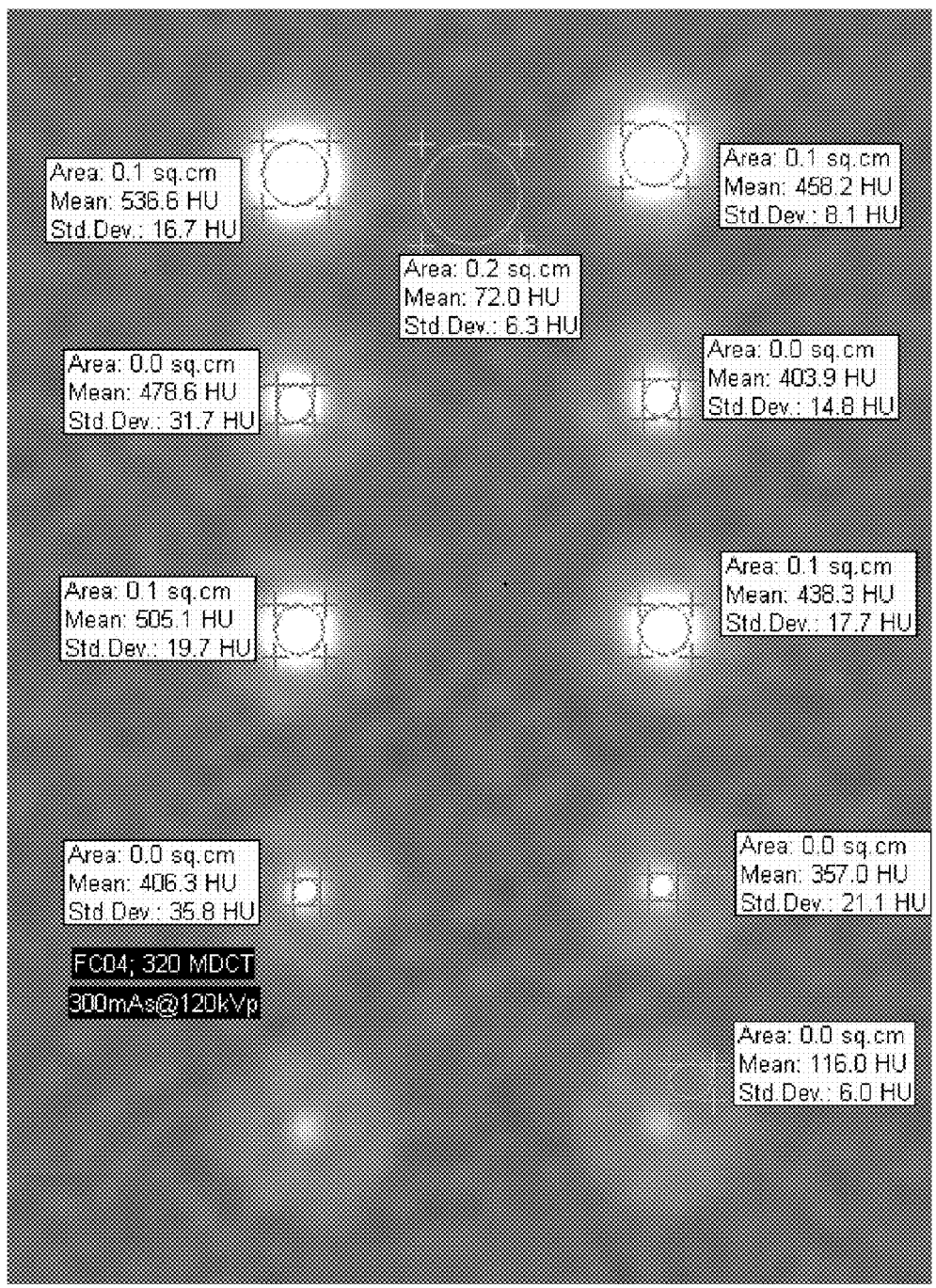
FIG. 6 illustrates reconstructed cross sectional CT images of the CV phantom demonstrating ROI placement within the vessel lumen, within the background medium (m) and on the vessel wall (w)

As shown in FIGS. 5A, 5B, and 6, the CT number in HU and the image noise, expressed as the standard deviation (Std Dev) in HU, were measured from the circular regions of interest (ROI) selected on reconstructed images. Standard tools available on the viewing workstations were used for these measurements. The ROI were kept at 80% of the cross-sectional area of the visible objects in acquired images from both phantoms. These ROI were accurately copied, using a "copy and paste" function, on all images between series, so that the area and location of these ROI remained the same for different series. Due to ROI size limitations, a crosshair point measurement tool was used for the objects of 1 mm or smaller in diameter.

A series of 26 ROI were placed on reconstructed images of the plaque phantom. The CT number and standard deviation values for each of the five cylindrical pearls (0.5-5 mm) within each of the five density-groups 50-800 mg HA/cm3 were measured. The tissue equivalent background density of this phantom was used as a reference value and measured at a fixed location in all of the reconstructed images with ROI size kept at 1.28 cm$^2$.

The normalization factor (f) of the scanner expressed in HU per mg/cm3 was calculated from the measured density in CT number (DHA) in HU from an ROI of 0.64 cm$^2$ placed within the Calcium Hydroxyapatite (HA) and a second density measured in CT number ($D_{Water}$) from a ROI in the water calibration cylinders, using the following formula:

$$f=(DHA-D_{Water})/c \quad (1)$$

where c=186 mg/cm3 is the density calibration factor of HA. In addition, the absolute density ($D_{abs}$) values in HU were calculated for each of the measured plaque densities ($D_{Plaque}$) in HU by applying the following formula:

$$D_{abs}=(D_{Plaque}-D_{Water})/f \quad (2)$$

This calibration function allows normalization of the measured CT numbers in HU with respect to physical density ρ (mg/cm$^3$).

Cross sectional CT images of the CV phantom were reconstructed to display the vessel lumen (FIG. 6). Individual ROI were placed within the contrast filled lumen for each vessel and the CT number [HU] was recorded. Two additional ROI were placed to measure the HU for the tissue equivalent background medium. Each ROI was kept to 80% of the vessel cross-sectional area.

For each phantom, the calculated absolute CT number ($D_{abs}$) in HU of each object was compared to the measured CT number of the largest reference object ($D_{abs, reference}$) within the phantom in order to calculate the percentage CT number reduction ($D_{relative}$) according to the following equation:

$$D_{relative}[\%]=D_{abs}/D_{abs,reference} \quad (3)$$

The relative CT number reduction value of each object was analyzed against the object diameter, d [mm] with both phantoms.

The true densities values described in the phantom specifications are the physical attenuation properties of the object's material. On an ideally calibrated CT scanner the measured density of water ($D_{Water}$) will equal zero. Therefore, using Equation 1, the normalization factor (f) would also equal 1. By substituting these values into Equation 2 ($D_{abs}$= ($D_{plaque}$−0)/1) the calculated absolute CT number would equal the true value of the object. However, in reality, there may be a small inaccuracy in the CT measurement of HU so, for example, the HU for water may not be measured exactly as zero. Consequently, the same situation applies to the density measurement of all other objects in the phantom. Therefore, in this study, the measured density value of the largest object, i.e., $D_{abs,reference}$ is used to normalize the $D_{relative}$[%] values. This method provides a realistic mathematic reduction factor for the specific CT being studied.

A sample dataset of measured CT number obtained from ROI placement on the Calcium Hydroxapatite (CaHA) cylinders (50, 100, 200, 400 and 800 mg/cm3), with image reconstruction using filter kernels FC02, FC04, FC05 and FC50 is shown in Table I. In particular, Table I shows the absolute ($D_{abs}$) and relative ($D_{relative}$) CT numbers for the CaHA cylinders contained within the plaque phantom used in Test 1 and Test 2. The CaHA cylinders are of variable nominal density (50, 100, 200, 400 and 800 mg/cm$^3$) and diameter (0.5, 1, 2, 3, 4 and 5 mm). $D_{abs}$ and $D_{relative}$ were calculated for each measured $D_{plaque}$ for all cylinders by applying Equations 2 and 3, respectively. The results demonstrated a comparable pattern of reduction in $D_{relative}$ values in relation to the cylinder diameter (d) in the plaque phantom.

Figure 7A:
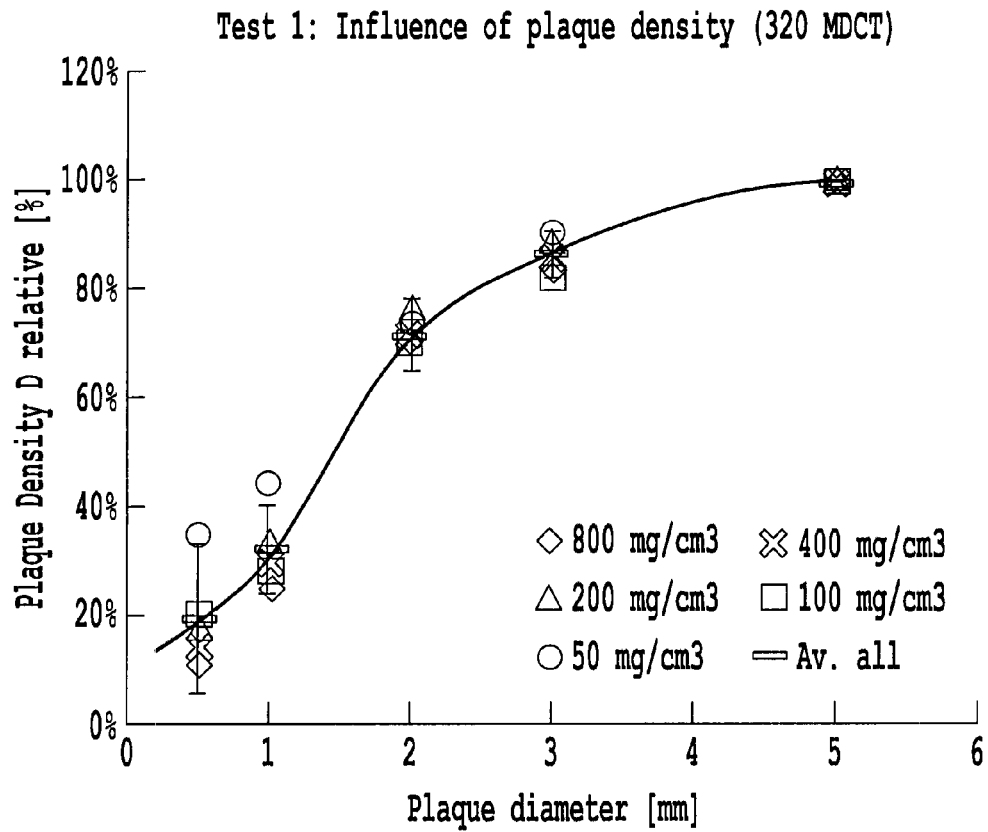
FIGS. 7A and 7B show the percentage plaque densities of 50-800 mg/cm$^3$ cylinder groups plotted against the object diameter using mean values over four filter kernels FC02, FC04, FC05, FC50 for (a) 320 MDCT and (b) 64 MDCT (Test 1)
Figure 7B:
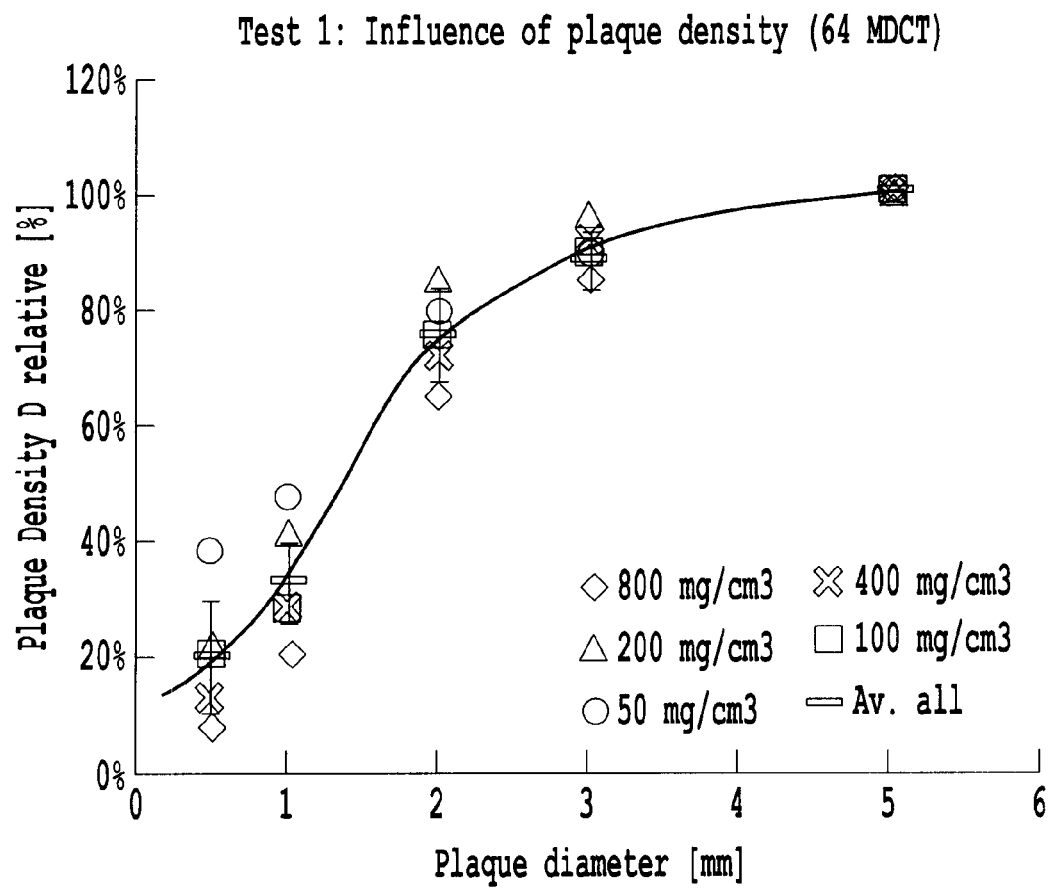
Figure 8A:
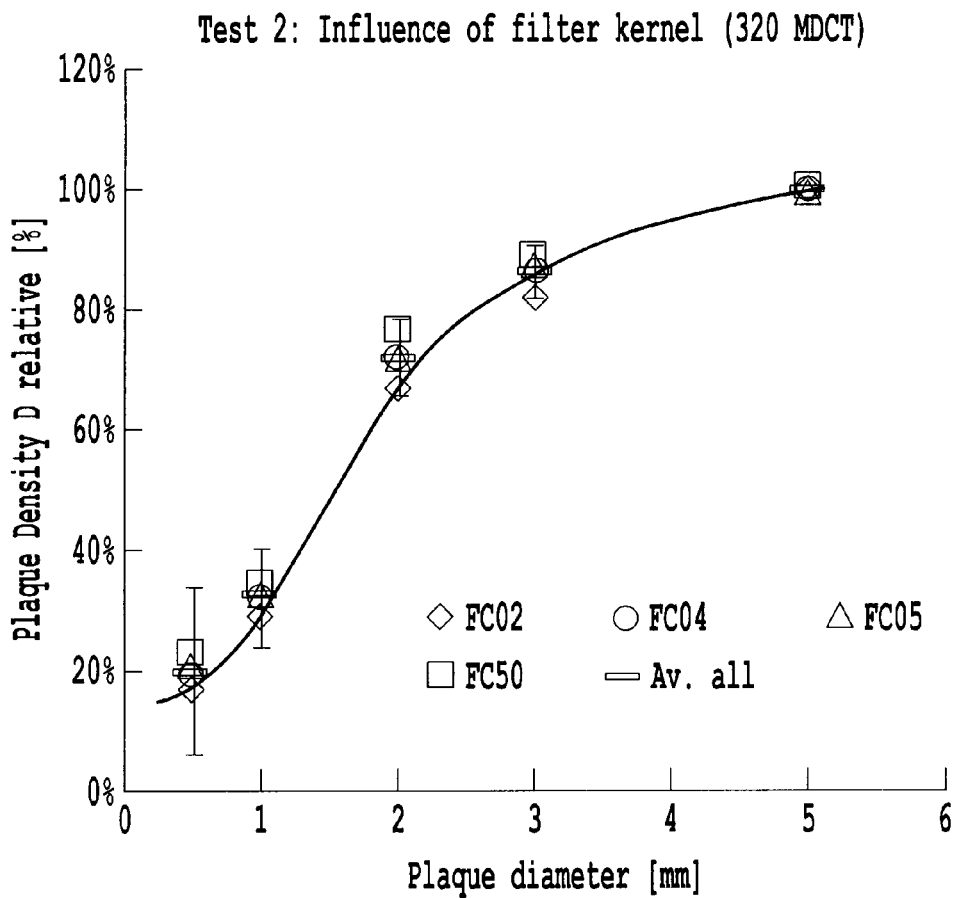
FIGS. 8A and 8B show the percentage plaque CT-density after reconstruction with four filter kernels plotted against the object diameter using mean values over all plaque densities (50-800 mg/cm3) for (a) 320 MDCT) and (b) 64 MDCT 1 (Test 2)
Figure 8B:
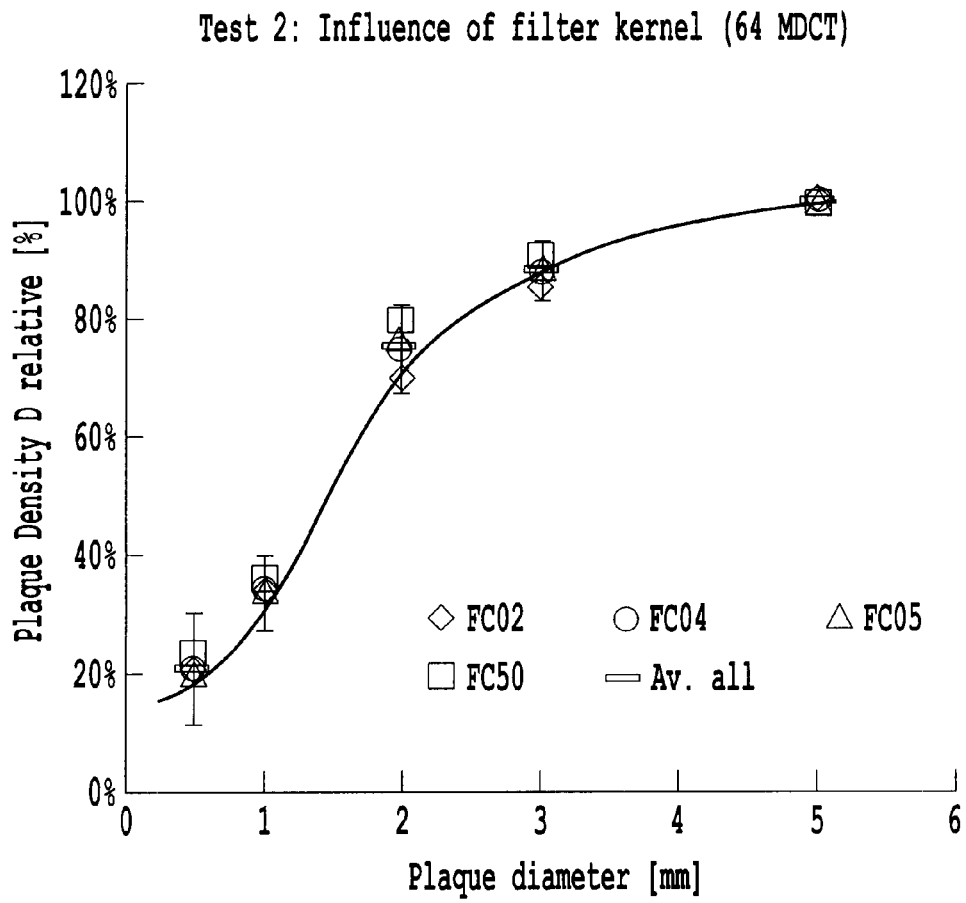

The variation in calculated $D_{relative}$ values of the CaHA cylinders with plaque density and diameter is shown in FIG. 7a (for 320 MDCT) and FIG. 7b (for 64 MDCT). Every plotted value of plaque density (50-800 mg/cm3) was averaged over the four filter kernels (FC02, FC04, FC05, FC50) for each CaHA cylinder diameter. The discrepancy between $D_{relative}$ and $D_{abs}$ values is similar for the 320 MDCT (FIGS. 7a) and 64 MDCT units (FIG. 7b). The spread of these mean values is higher for the smaller objects with lower physical densities because a greater reduction in measured CT number occurs at smaller diameters and consequently these small densities blend into the tissue equivalent background which has similar CT numbers. In addition, the accuracy of CT number measurement for plaque sizes near to 0.5 mm in diameter is reduced due to the limitations in minimal ROI size. FIGS. 8A and 8B demonstrate mean relative plaque density measured in HU for every filter kernel (FC02, FC04, FC05, FC50) averaged for all CaHA cylinders (50-800 mg/cm3) at each cylinder diameter. As in FIGS. 7a and 7b, the discrepancy between measured $D_{abs}$ and nominal $D_{abs,reference}$ values is similar for the 320 MDCT (FIGS. 8a) and 64 MDCT units (FIG. 8b) and the spread increases with smaller object diameter for the same reason as in Test 1.

Figure 9A:
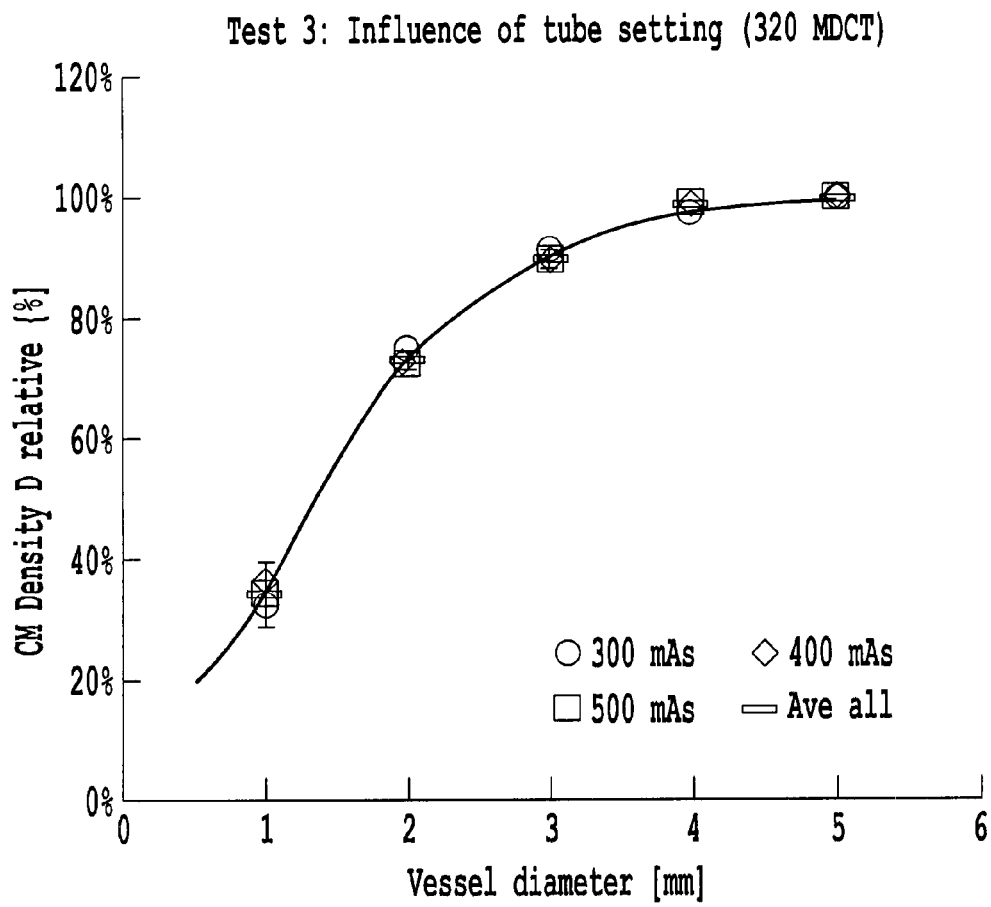
FIGS. 9A and 9B illustrate (a) Percentage lumen CT-density for 370 mg/ml CM plotted against vessel diameter and scanned at three different tube settings 300, 400, 500 mAs, and (b) Percentage lumen CT-density of 320 and 370 mg/ml CM plotted against the vessel diameter scanned with 300 mAs.

The CV phantom was initially scanned at three different tube settings: 300, 400 and 500 mAs at a constant tube potential of 120 kVp (Test 3) and images were reconstructed with a single filter kernel (FC04) in order to determine the influence of tube settings on measured lumen CT number with vessel diameter. A sample dataset of measured lumen CT number from Test 3 is shown in Table II. In particular, Table II shows a sample of CV Phantom dataset scanned with three levels of tube current settings (Test 3, 320 MDCT), and shows measured CT numbers with calculated $D_{relative}$ values for vessel diameters of 1 mm to 5 mm. All vessels filled with CM of 370 mg/ml from 1-5 mm. These data reveal that the measured lumen CT numbers decrease with vessel diameter, but are relatively stable with variation in X-ray exposure (FIG. 9a).

Figure 9B:
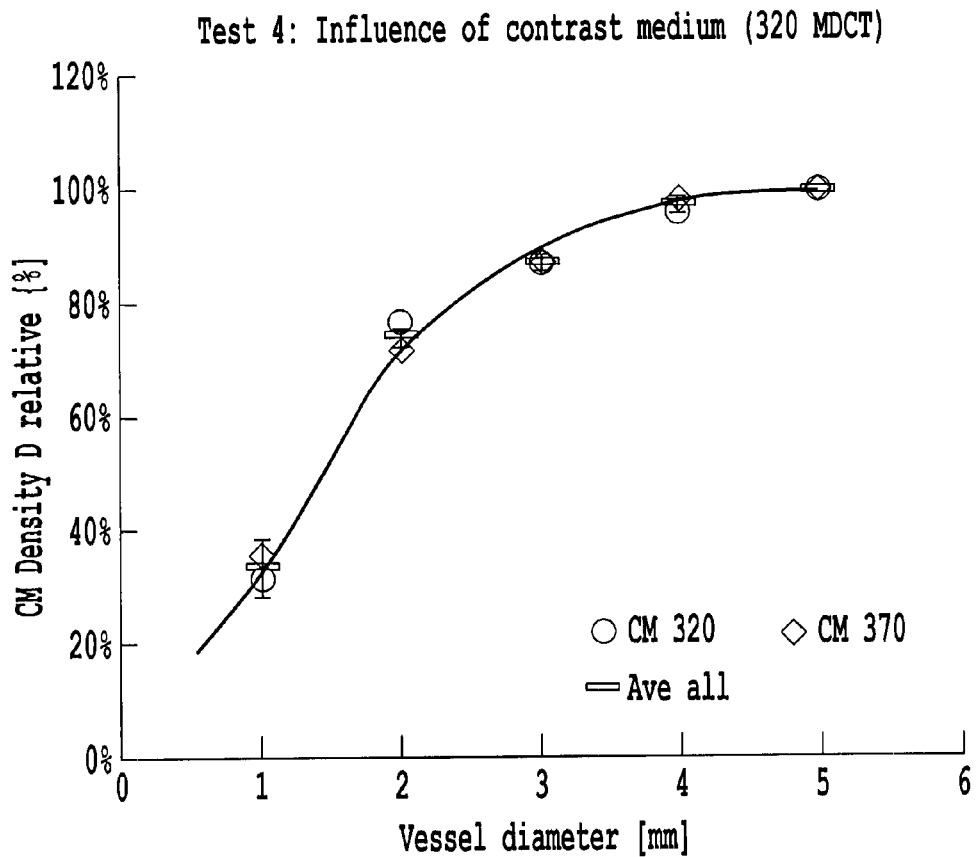

Subsequent evaluation of the CV phantom involved filling the two sets of vessel tubes with two different concentrations of iodinated contrast media, 320 and 370 mg/ml, scanning the phantom at a fixed tube setting with 300 mAs and 120 kV, reconstructing the images with filters FC04 (low spatial frequency filter) and measuring the variation of luminal CT-density with lumen diameter (Test 4). The results in FIG. 9b confirm that the reduction in measured luminal CT-density values with luminal diameter is independent of contrast density.

A total of 300 measurements of CT number were obtained from both phantoms and analyzed. The measured data from all the CT scanners (as shown in Table III) was averaged and plotted against the object diameter consecutively to determine the relationship between the parameters under observation. In particular, Table II shows pooled data obtained from scanning both phantoms on 64 and 320 MDCT. The relative percentage CT number values are compared with the natural logarithmic values [ln(d)] of the object's diameter and the derived values were used to determine the mathematical correction function.

In these experiments, the calibrations were normalized to an object size of 5 mm, the largest object diameter in either phantom. It was concluded that the reconstruction filter kernels FC02, FC04, FC05, and FC50 on both 64 MDCT and 320 MDCT showed comparable percentage reduction of measured CT number values with reduction in object diameter.

The conclusion made from both phantoms tests was that the percentage reduction in measured CT number ($D_{relative}$) is only influenced by object size that is, in our case, plaque or vessel diameter (d).

The study concludes two asymptotical limits for the maximum and minimum measured CT numbers for each density group. The 100% maximum limit of the function is defined for the measured HU values of larger objects (objects with larger diameter than 5 mm) where the size effect diminishes. And the minimum limit of the function is defined by the HU values of extremely small objects (0.1 mm in diameter with density of 50 HU) where it blends into tissue equivalent background density values. This observation, in combination with limited CT in-plane resolution (in our case 0.35 mm×0.35 mm), means that objects of such a small diameter would merge into the background noise.

By considering these physical conditions and using the well known fundamental physical law that the absorption of an object is proportional to exp ($-\mu*d$); where $\mu$ is the mean attenuation coefficient and d is the diameter of the object [10], a mathematical function of the form is used to derive an asymptotical curve-fitted regression function from the collected data.

$$D_{relative}[\%] = 1 - c*\exp(-a*d^b) \quad (4)$$

The resultant expression for $D_{relative}$ [%] has free adjustable variables a, b, and c, which are calculated by a non-linear regression method.

Figure 10:
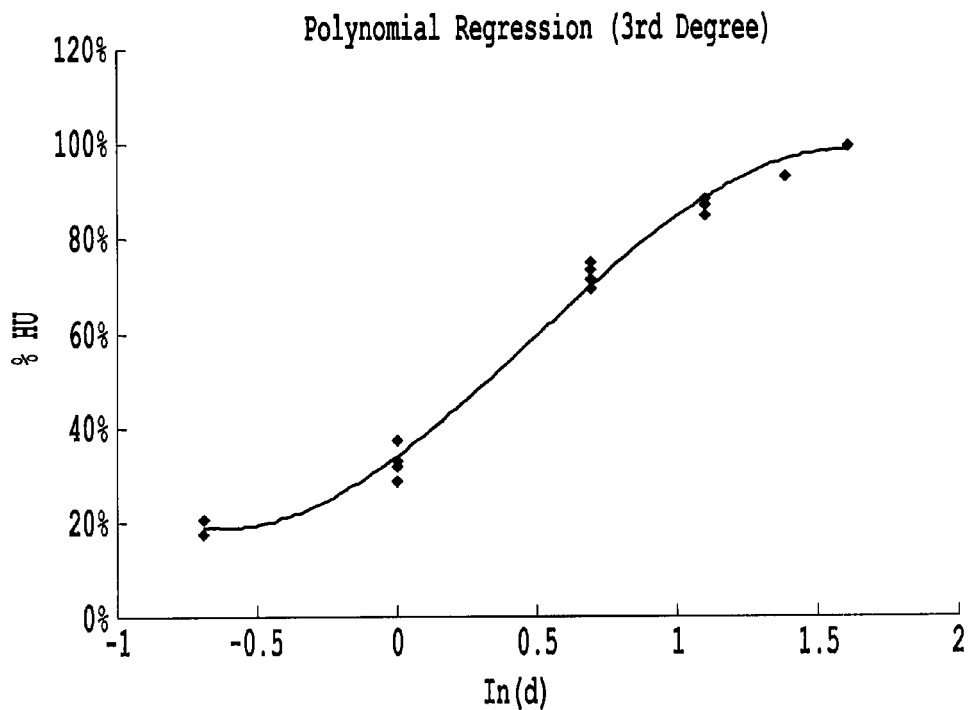
FIG. 10 shows the model function and the correlation between the measured $D_{relative}$ and ln(d) of axial object diameter d.
Figure 11:
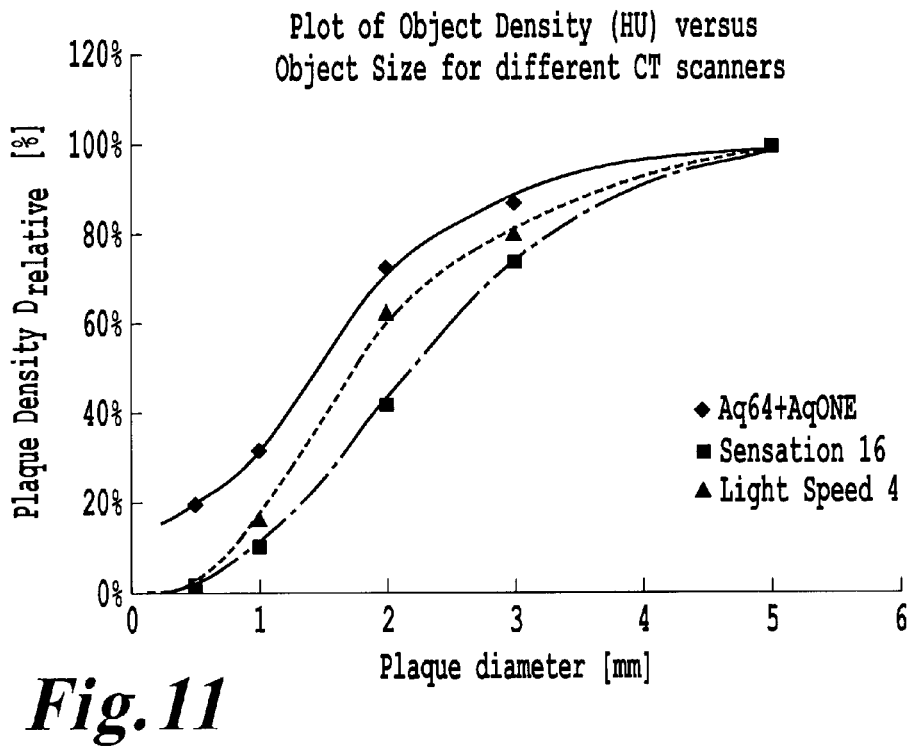
FIG. 11 is a comparison of object CT-density with plaque size for three different CT scanners using standard cardiac reconstruction algorithms and the plaque phantom.

In order to improve graphical visualization of the smaller objects, logarithmic transformation ln(d) of the object diameter d was used for x-axis. The resulting plot of $D_{relative}$ derived values from Eq. 4 along with the $D_{relative}$ data obtained from all the scanners (using Eq. 3) is shown in FIG. 10. Analysis of the Eq. 4 showed a best fit with low StdError=0.000979 and high R-value $R^2$=0.999818.

It was concluded that for the four established filter kernels used in CTA the CT number correction for small objects can be performed based on object diameter. Because of the clear mathematical correlation with circular objects, the cross sectional area also can be used. The x-ray exposure parameters and inherent density of the objects itself has no influence on this relation.

There was no difference in the correction function for the three CT scanners used in this study as they are manufactured by the same vendor, use similar CT reconstruction algorithms and gantry designs.

A preliminary evaluation of $D_{relative}$ values for the plaque phantom was also carried out on two additional MDCT units manufactured by other vendors. FIG. 10 displays the data from these additional MDCT units compared to the results from the 64 and 320 MDCT units used in this study. There is a similar trend of reduction in $D_{relative}$ with object size, however, as $D_{relative}$ values were lower for the additional MDCT units, separate mathematical correction functions will be required for these units, using the principles outlined herein.

TABLE I

| Structures material (HA) | Plaque phantom ROI number | Insert diameter mm | FC02 $D_{abs}$ HU | FC02 $D_{relative}$ [%] | FC04 $D_{abs}$ HU | FC04 $D_{relative}$ [%] | FC05 $D_{abs}$ HU | FC05 $D_{relative}$ [%] | FC50 $D_{abs}$ HU | FC50 $D_{relative}$ [%] | Mean (FC02, 04, 05, 50) $D_{relative}$ [%] | Std dev (FC02, 04, 05, 50) $D_{relative}$ [%] |
|---|---|---|---|---|---|---|---|---|---|---|---|---|
| 800 mg/cm3 | 1 | 0.5 | 68.2 | 8.3% | 89.9 | 10.6% | 99.1 | 11.6% | 122.3 | 14.6% | 11.3% | 2.6% |
| | 2 | 1 | 189.6 | 23.2% | 200.9 | 23.6% | 211.9 | 24.8% | 240.9 | 28.8% | 25.1% | 2.6% |
| | 3 | 2 | 508.3 | 62.2% | 580.5 | 68.2% | 599.0 | 70.0% | 649.0 | 77.6% | 69.5% | 6.4% |
| | 4 | 3 | 648.8 | 79.3% | 708.1 | 83.1% | 720.4 | 84.1% | 741.3 | 88.6% | 83.8% | 3.8% |
| | 5 | 5 | 817.7 | 100.0% | 851.8 | 100.0% | 856.2 | 100.0% | 836.4 | 100.0% | 100.0% | 0.0% |
| 400 mg/cm3 | 6 | 0.5 | 40.0 | 11.1% | 52.4 | 13.9% | 57.8 | 15.2% | 64.4 | 16.1% | 14.1% | 2.2% |
| | 7 | 1 | 99.8 | 27.6% | 115.5 | 30.6% | 121.9 | 32.1% | 123.5 | 30.8% | 30.3% | 1.9% |
| | 8 | 2 | 230.7 | 63.8% | 255.6 | 67.7% | 266.7 | 70.2% | 291.6 | 72.7% | 68.6% | 3.8% |
| | 9 | 3 | 297.6 | 82.3% | 324.7 | 86.0% | 330.5 | 87.0% | 354.3 | 88.3% | 85.9% | 2.6% |
| | 10 | 5 | 361.7 | 100.0% | 377.4 | 100.0% | 379.9 | 100.0% | 401.1 | 100.0% | 100.0% | 0.0% |
| 200 mg/cm3 | 11 | 0.5 | 28.4 | 15.7% | 32.1 | 17.6% | 36.8 | 20.2% | 40.7 | 20.4% | 18.5% | 2.3% |
| | 12 | 1 | 54.4 | 30.0% | 62.4 | 34.2% | 65.8 | 36.1% | 63.8 | 32.0% | 33.1% | 2.6% |
| | 13 | 2 | 139.9 | 77.3% | 137.0 | 75.1% | 142.4 | 78.2% | 152.5 | 76.5% | 76.8% | 1.3% |
| | 14 | 3 | 157.7 | 87.2% | 166.7 | 91.4% | 173.7 | 95.4% | 178.3 | 89.4% | 90.8% | 3.5% |
| | 15 | 5 | 180.9 | 100.0% | 182.3 | 100.0% | 182.1 | 100.0% | 199.5 | 100.0% | 100.0% | 0.0% |
| 100 mg/cm3 | 16 | 0.5 | 20.9 | 17.0% | 23.9 | 18.8% | 27.0 | 21.1% | 26.4 | 24.8% | 20.4% | 3.4% |
| | 17 | 1 | 30.5 | 24.7% | 34.1 | 26.8% | 36.2 | 28.3% | 32.9 | 31.0% | 27.7% | 2.6% |
| | 18 | 2 | 79.5 | 64.6% | 88.1 | 69.3% | 90.9 | 70.9% | 83.0 | 78.1% | 70.7% | 5.6% |
| | 19 | 3 | 95.4 | 77.5% | 102.1 | 80.3% | 104.5 | 81.6% | 93.3 | 87.8% | 81.8% | 4.3% |
| | 20 | 5 | 123.1 | 100.0% | 127.1 | 100.0% | 128.1 | 100.0% | 106.3 | 100.0% | 100.0% | 0.0% |
| 50 mg/cm3 | 21 | 0.5 | 20.1 | 32.1% | 23.1 | 36.8% | 21.4 | 33.0% | 20.8 | 39.5% | 35.4% | 3.4% |
| | 22 | 1 | 25.5 | 40.8% | 27.5 | 43.8% | 29.7 | 45.9% | 25.8 | 48.9% | 44.8% | 3.4% |
| | 23 | 2 | 42.5 | 68.0% | 50.5 | 80.3% | 46.8 | 72.3% | 40.7 | 77.2% | 74.4% | 5.4% |
| | 24 | 3 | 53.5 | 85.7% | 57.0 | 90.7% | 58.4 | 90.1% | 50.1 | 95.0% | 90.4% | 3.8% |
| | 25 | 5 | 62.5 | 100.0% | 62.8 | 100.0% | 64.8 | 100.0% | 52.68 | 100.0% | 100.0% | 0.0% |

| 320 MDCT | 120 kVp | Pitch 41 | CTDIvol-e | WL = 80 |
| | 400 mA, 1.5 sec | FOV small | 192 mGy | WW = 150 |
| | 600 mAs | | | |

TABLE II

| CM 370 mg/ml Rot. time = 1 sec | 120 kVp, 300 mAs | | | 120 kVp, 400 mAs | | | 120 kVp, 500 mAs | | | | STD |
|---|---|---|---|---|---|---|---|---|---|---|---|
| FC04 vessel diameter | HU | STD | $D_{relative}$ [%] | HU | STD | $D_{relative}$ [%] | HU | STD | $D_{relative}$ [%] | $D_{relative}$[%] All mAs | $D_{relative}$[%] All mAs |
| 1 mm | 185.2 | | 32.3% | 215.6 | | 36.5% | 201.3 | | 34.1% | 34.3% | 2.10% |
| 2 mm | 431.5 | 32.2 | 75.4% | 424.9 | 34.0 | 72.0% | 426.7 | 38.9 | 72.3% | 73.2% | 1.86% |
| 3 mm | 522.3 | 10.8 | 91.2% | 524.7 | 9.9 | 88.9% | 528.6 | 13.9 | 89.5% | 89.9% | 1.20% |
| 4 mm | 559.1 | 7.0 | 97.6% | 584.3 | 6.8 | 99.0% | 584.6 | 10.7 | 99.0% | 98.5% | 0.78% |
| 5 mm | 572.6 | 10.6 | 100.0% | 590.2 | 4.9 | 100.0% | 590.5 | 6.2 | 100.0% | 100.0% | 0.00% |

TABLE III

Data set for model function calculation

| CT/Phantom | Diameter | ln(d) | Drelative[%] |
|---|---|---|---|
| 64 MDCT1 Plaque Phantom | 0.5 | −0.693 | 20.8% |
| | 1 | 0.000 | 33.7% |
| | 2 | 0.693 | 75.2% |
| | 3 | 1.099 | 88.3% |
| | 5 | 1.609 | 100.0% |
| 64 MDCT2 Plaque Phantom | 0.5 | −0.693 | 17.5% |
| | 1 | 0.000 | 29.2% |
| | 2 | 0.693 | 69.7% |
| | 3 | 1.099 | 85.1% |
| | 5 | 1.609 | 100.0% |
| 320 MDCT Plaque Phantom | 0.5 | −0.693 | 20.7% |
| | 1 | 0.000 | 32.2% |
| | 2 | 0.693 | 71.8% |
| | 3 | 1.099 | 87.4% |
| | 5 | 1.609 | 100.0% |
| 320 MDCT Vessel phantom | 1 | 0.000 | 37.9% |
| | 2 | 0.693 | 73.7% |
| | 3 | 1.099 | 88.5% |
| | 4 | 1.386 | 93.4% |
| | 5 | 1.609 | 100.0% |

The 5 mm diameter is taken as the normalization object for Equation 3 because, at this size, the reduction in measured CT number is significantly low and the measured $D_{relative}$ [%] values almost reach to the asymptote. For the 5 mm diameter objects (largest in both the phantoms), Equation 4 predicts 99.69% ($D_{relative}$ [%]) values of the max HU value that can possibly be measured from a very large structure of a given density. The predicted relative CT numbers approaches to 100% for the objects of 7 mm in diameter or larger.

The above-described experiments are limited by the evaluation of only three CT units, all from the same manufacturer. There was no observed data variance between the two 64 MDCT units or the 320 MDCT as the detectors were identical in physical dimensions and composition. A preliminary evaluation of two additional CT units, each from different manufacturers, demonstrated a similar pattern of reduction in measured CT numbers (HU) with the reduction in object size, but the actual value of the mathematical correction function differed for each unit and would need to be individually calculated using the methodology and a standard phantom as outlined in this study. In addition, we only evaluated the results for the four reconstruction filter kernels that the manufacturer has recommended for plaque quantification. It is possible that alternate reconstruction filter kernels with different properties could produce a different mathematical model. However, we believe that object diameter would remain the predominant influence on measured object CT numbers.

Determination of plaque composition using computed tomography is limited due to the small size (diameter or cross-sectional area) of vessel plaque. The present inventors have derived a mathematical function that can compensate for these limitations and generate accurate characterization of plaque composition and size. This relationship is applied to the evaluation of arterial plaque, risk stratification, and assessment of treatments that target reductions in the volume of non-calcified plaque.

The rapid development of multi-detector CT imaging (MDCT) has facilitated the detection of smaller objects. However, the correct characterization of these objects is compromised by the inherent limitations of CT technology. The mathematical correction function described above is used as part of a process to correct for the inherent limitations of MDCT so as to produce a correct density measurement of the object. As described in more detail below, the process involves calibration of the CT unit model and verification and adjustment of the variable parameters to fit the characteristics of the CT unit. A calibration phantom similar used in the experiments described above allows for the determination of the percentage reduction in CT number due to objection size and the determination of a correction function.

The method can be applied to an image using either a region of interest in a manual method of improvement, or using an automated algorithm that applies the correction to all parts of the image in conjunction with a segmentation algorithm.

Figure 12:
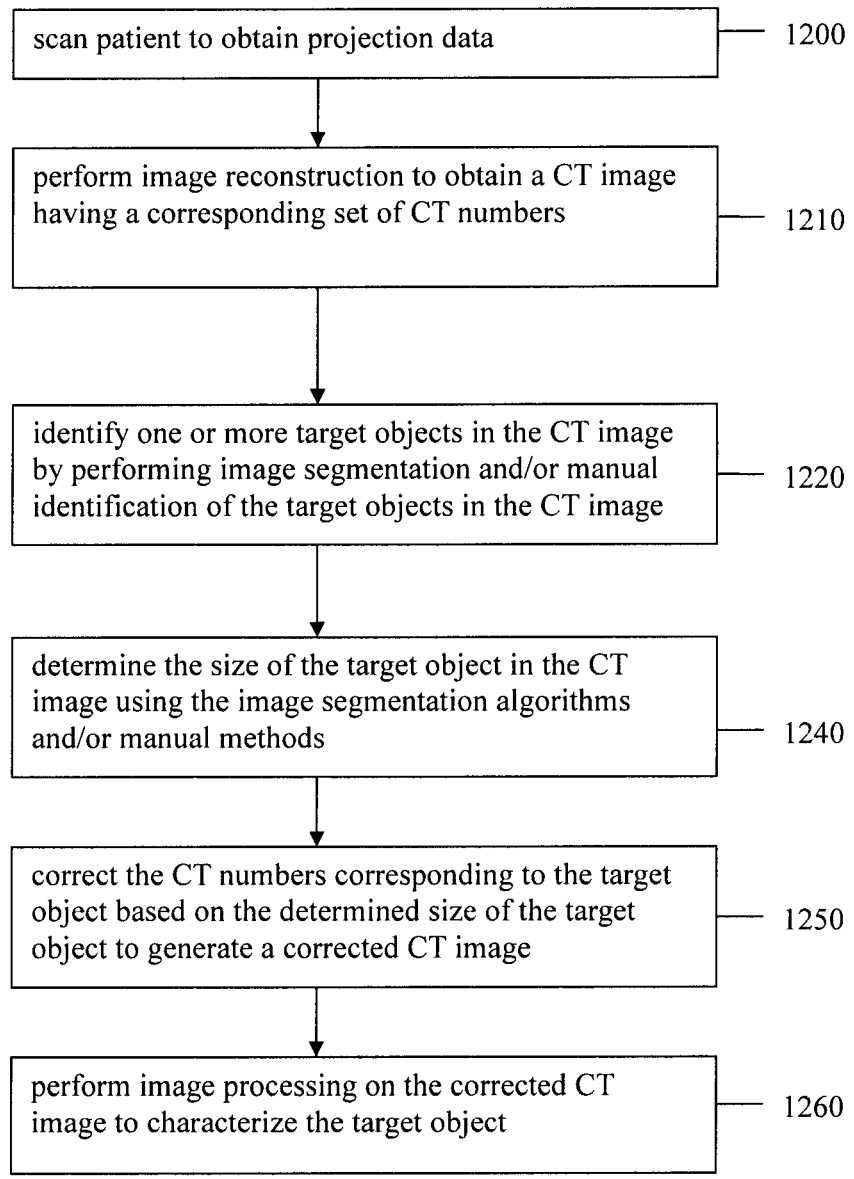
FIG. 12 illustrates a flowchart of a method of correcting CT numbers in a CT image.

In particular, FIG. 12 illustrates a method of correcting the CT numbers corresponding to a target object in a CT image or volume using the correction function of Equation 4 or other similar equation.

In step 1200, a patient is scanned using a MDCT scanner to obtain projection data.

In step 1210, image reconstruction is performed to obtain one or more CT images or volume date. The reconstruction algorithms mentioned above, as well as other reconstruction algorithms, can be used to obtain the CT images. Each CT image is represented by a set of CT numbers (in HU).

Steps 1200 and 1210 can be performed at any time prior to the performance of the remaining steps illustrated in FIG. 12. For example, CT images can be stored in a computer server on a network for later processing according to this method.

In step 1220, one or more target objects are identified in the CT image or volume using image segmentation of the CT image or manual identification by an operator of target objects, or a combination of automatic and manual methods. Examples of segmentation software that can be used in this step include CardIQ™ Analysis and SmartScore (General Electric), syngo InSpace 4D Advanced Vessel Analysis, and Sureplaque™ (Toshiba). The target object can be an area or volume within the CT image or volume and can be set by a user or found automatically by a segmentation algorithm, such as those mentioned above. In one embodiment, one or more target objects, such as arterial plaque or lesions within the liver are identified automatically using image processing techniques using volume rendering software algorithms.

In step 1240, the target objects identified in step 1220 are measured to determine their size. The size can be the effective diameter of the target object. Alternatively, the cross-sectional area or volume of the target object can be used as the size variable. The measurement of the size of each target object can be performed automatically by using image processing techniques, such as those provided with the software packages mentioned above, or can be performed manually by the operator.

In step 1250, Equation 4 is used to correct the mean CT numbers of each target region with the resulting correction function. For example, for a target object having a geometric size d (e.g., diameter), Equation 4 gives the percentage CT number reduction for that target object region of interest. Thus, in step 1250, the CT numbers associated with the target object are increased to offset the decrease determined by Equation 4. For example, if Equation 4 determines a percentage CT number reduction of 50% based on the diameter of an identified target object, the CT numbers of the target object are increased by a factor of two. In one embodiment, the data of the CT image or volume is modified for each target object so that a modified CT image or volume is generated and displayed.

In step 1260, the corrected CT image or volume data is used to characterize the target objects using various automated or manual image processing or diagnostic techniques. For example, determining whether a target object is lipid-based plaque or fibrous plaque is performed in this step.

The method shown in FIG. 12 can be applied to any CT application in which correct density measurements are required of objects less than or equal to 5 mm, and include, but are not limited to, the following objects: arterial plaque, lesions within the liver, pancreas, kidneys, and brain, and musculoskeletal lesions. Any image that has small objects such as vasculature or lesions can be affected by surrounding material in determining the CT number. Also for Dual-Energy (DE) applications, the free parameters a, b, and c in Equation 4 can vary with tube voltage. The accuracy of DE applications is currently limited by object size. The CT number correction calculated separately for every tube voltage leads to an improvement of DE information (e.g., for kidney and renal stones). Accurate assessment of the HU value will help in clinical diagnosis of disease, such as coronary plaque characterization, which will help differentiate between lipid-based plaque and fibrous plaque.

The CT number correction method shown in FIG. 12 can also influence an image processing algorithm by improving the segmentation or characterization algorithm associated with the image processing algorithm. This will help to accurately determine the size of small lesions or vasculature and generate an accurate value to be used by a diagnostic application. For example, a kidney stone may need to be accurately sized to determine treatment. The size of the kidney stone as well as the lumen of the ureter leading away from the kidney need to be accurately sized to determine if the stone will pass through, or if a procedure needs to be completed to decrease the size of the stone. Another example is the determination of stenosis within small vessels such as the principal coronary arteries or within the major branches such as the diagonals.

Figure 13:
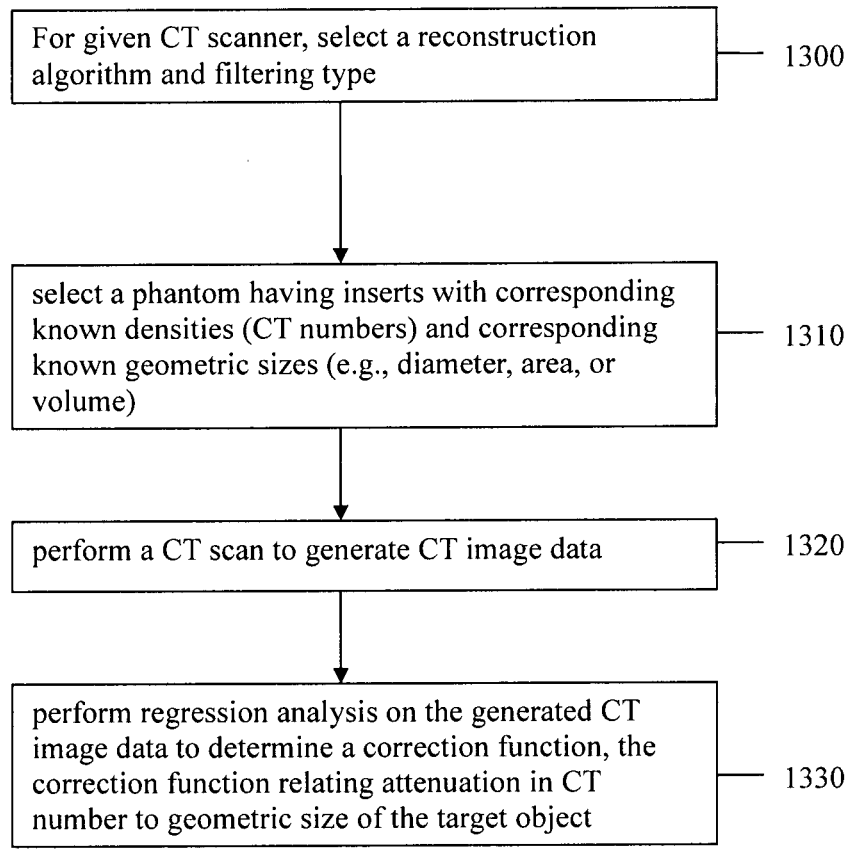
FIG. 13 illustrates a method of determining a correction function for correcting CT numbers of a target object in a CT image obtained using a given CT scanner.

FIG. 13 illustrates a method of determining a correction function for correcting computed tomographic (CT) numbers of a target object in a CT image obtained using a CT scanner, based on a geometric size of the target object.

In step 1300, a reconstruction algorithm and filtering type for use with the CT scanner are selected or set.

In step 1310, one or more phantoms are selected, each phantom having one or more inserts of known density (CT number) and geometric size. See, e.g., the plaque phantom and the cardiovascular phantoms described above.

In step 1320, a CT scan of the phantom is performed to generate image data. Note that steps 1310 and 1320 can be repeated for multiple phantoms. Further, as discussed above, these steps can be repeated for various filter kernels and tube settings to generate additional sets of CT image or volume data.

In step 1330, nonlinear regression analysis is performed on the generated CT image or volume data to determine a correction function, such as that shown in Equation 4. In one embodiment, the parameters a, b, and c are determined for the correction function shown Equation 4. The parameters a, b, and c are expected to vary by CT scanner model, reconstruction algorithm, and filter type, but are independent of tube voltage and filter kernel, as discussed above. Other forms of the correction function having other parameters are possible. The correction function determined in step 1330 can be used to correct CT numbers of target objects in a CT image, as discussed with respect to FIG. 12.

Figure 14:
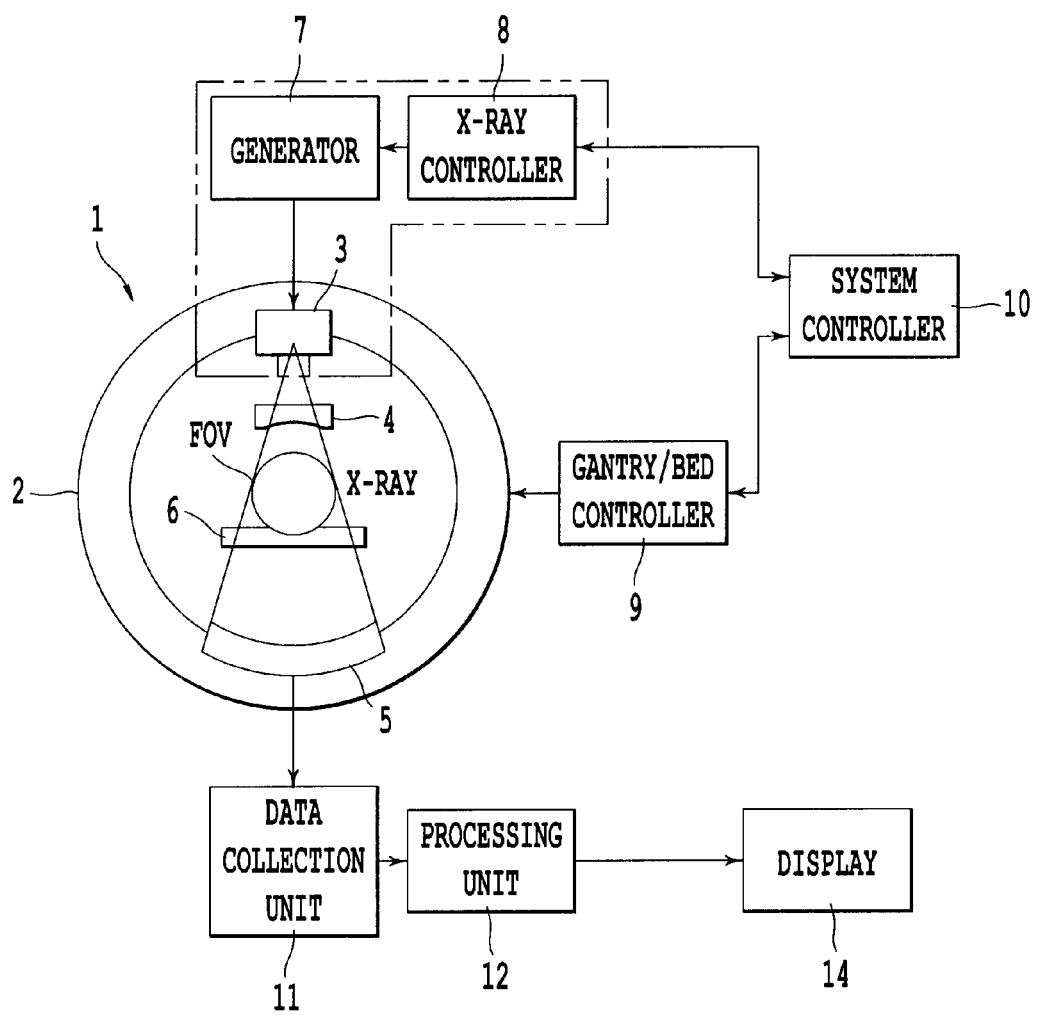
FIG. 14 illustrates a CT apparatus and processing unit to implement a system for determining a correction function for correcting CT numbers of a target object in a CT image obtained using the CT apparatus, and a system for correcting CT numbers in a CT image using the correction function.

FIG. 14 shows an X-ray computed-topographic imaging device that can be used to obtain data that is processed by methods described herein. The projection data measurement system constituted by gantry 1 accommodates an X-ray source 3 that generates a cone-beam of X-ray flux approximately cone-shaped, and a two-dimensional array type X-ray detector 5 consisting of a plurality of detector elements arranged in a two-dimensional fashion, i.e., a plurality of elements arranged in one dimension stacked in a plurality of rows. X-ray source 3 and two-dimensional array type X-ray detector 5 are installed on a rotating ring 2 in facing opposite sides of a subject or phantom, which is laid on a sliding sheet of a bed or platform 6. Two-dimensional array type X-ray detector 5 is mounted on rotating ring 2. Each detector element corresponds to one channel. X-rays from X-ray source 3 are directed on to subject through an X-ray filter 4. X-rays that have passed through the subject are detected as an electrical signal by two-dimensional array type X-ray detector 5.

X-ray controller 8 supplies a trigger signal to high voltage generator 7. High voltage generator 7 applies high voltage to X-ray source 3 based on the timing with which the trigger signal is received. This causes X-rays to be emitted from X-ray source 3. Gantry/bed controller 9 synchronously controls the revolution of rotating ring 2 of gantry 1 and the sliding of the sliding sheet of bed 6. System controller 10 constitutes the control center of the entire system and controls X-ray controller 8 and gantry/bed controller 9 such that, as seen from the subject, X-ray source 3 executes so-called helical scanning, in which the X-ray source moves along a helical path. Specifically, rotating ring 2 is continuously rotated with fixed angular speed while the sliding plate is displaced with fixed speed, and X-rays are emitted continuously or intermittently at fixed angular intervals from X-ray source 3.

The output signal of two-dimensional array type x-ray detector 5 is amplified by a data collection unit 11 for each channel and converted to a digital signal to produce projection data. The projection data that is output from data collection unit 11 is fed to processing unit 12. Processing unit 12 uses the projection data to find backprojection data reflecting the X-ray absorption in each voxel. In the helical scanning system using a cone-beam of X-rays, the imaging region (effective field of view) is a cylindrical shape with radius ω centered on the axis of revolution. Processing unit 12 defines a plurality of voxels in this imaging region, and finds the backprojection data for each voxel. The three-dimensional image data or tomographic image data compiled by using this backprojection data is sent to display device 14, where it is displayed visually as a three-dimensional image or tomographic image.

The processing unit 12 can be connected to one or more input devices (not shown). The processing unit can also be connected to various networks, including the Internet.

The processing unit 12 is configured to perform the regression analysis described above, including that described in step 1330 in FIG. 13. The processing unit is also configured to perform steps 1220 through 1260 for correcting a CT image as described above, as shown in FIG. 12. For example, software programs executed on the processing unit 12 allow an operator to manually identify a target object and determine the object's size. Alternatively, software programs executed on the processing unit 12 can automatically identify and measure the target objects.

The processing unit 12 can be implemented using a computer system. The computer system includes a bus or other communication mechanism for communicating information, and a processor coupled with the bus for processing the information. The computer system 1 also includes a main memory, such as a random access memory (RAM) or other dynamic storage device (e.g., dynamic RAM (DRAM), static RAM (SRAM), and synchronous DRAM (SDRAM)), coupled to the bus for storing information and instructions to be executed by processor. In addition, the main memory may be used for storing temporary variables or other intermediate information during the execution of instructions by the processor. The computer system further includes a read only memory (ROM) or other static storage device (e.g., programmable ROM (PROM), erasable PROM (EPROM), and electrically erasable PROM (EEPROM)) coupled to the bus for storing static information and instructions for the processor.

The computer system also includes a disk controller coupled to the bus to control one or more storage devices for storing information and instructions, such as a magnetic hard disk, and a removable media drive (e.g., floppy disk drive, read-only compact disc drive, read/write compact disc drive, compact disc jukebox, tape drive, and removable magneto-optical drive). The storage devices may be added to the computer system using an appropriate device interface (e.g., small computer system interface (SCSI), integrated device electronics (IDE), enhanced-IDE (E-IDE), direct memory access (DMA), or ultra-DMA).

The computer system may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system may also include a display controller coupled to the bus to control a display, such as a cathode ray tube (CRT), for displaying information to a computer user. The computer system includes input devices, such as a keyboard and a pointing device, for interacting with a computer user and providing information to the processor. The pointing device, for example, may be a mouse, a trackball, or a pointing stick for communicating direction information and command selections to the processor and for controlling cursor movement on the display. In addition, a printer may provide printed listings of data stored and/or generated by the computer system.

The computer system performs a portion or all of the processing steps of the invention in response to the processor executing one or more sequences of one or more instructions contained in a memory, such as the main memory. Such instructions may be read into the main memory from another computer readable medium, such as a hard disk or a removable media drive. One or more processors in a multi-processing arrangement may also be employed to execute the sequences of instructions contained in main memory. In alternative embodiments, hard-wired circuitry may be used in place of or in combination with software instructions. Thus, embodiments are not limited to any specific combination of hardware circuitry and software.

As stated above, the computer system includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, or any other medium from which a computer can read.

Stored on any one or on a combination of computer readable media, the present invention includes software for controlling the computer system, for driving a device or devices for implementing the invention, and for enabling the computer system to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices described herein may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor for execution. A computer readable medium may take many forms, including but not limited to, non-volatile media, and volatile media. Non-volatile media includes, for example, optical, magnetic disks, and magneto-optical disks, such as the hard disk or the removable media drive. Volatile media includes dynamic memory, such as the main memory.

Various forms of computer readable media may be involved in carrying out one or more sequences of one or more instructions to processor for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system may receive the data on the telephone line and use an infrared transmitter to convert the data to an infrared signal. An infrared detector coupled to the bus can receive the data carried in the infrared signal and place the data on the bus. The bus carries the data to the main memory, from which the processor retrieves and executes the instructions. The instructions received by the main memory may optionally be stored on storage device either before or after execution by processor.

The computer system also includes a communication interface coupled to the bus. The communication interface provides a two-way data communication coupling to a network link that is connected to, for example, a local area network (LAN), or to another communications network such as the Internet. For example, the communication interface may be a network interface card to attach to any packet switched LAN. As another example, the communication interface may be an asymmetrical digital subscriber line (ADSL) card, an integrated services digital network (ISDN) card or a modem to provide a data communication connection to a corresponding type of communications line. Wireless links may also be implemented. In any such implementation, the communication interface sends and receives electrical, electromagnetic or optical signals that carry digital data streams representing various types of information.

The network link typically provides data communication through one or more networks to other data devices. For example, the network link may provide a connection to another computer through a local network (e.g., a LAN) or through equipment operated by a service provider, which provides communication services through a communications network. The local network and the communications network use, for example, electrical, electromagnetic, or optical signals that carry digital data streams, and the associated physical layer (e.g., CAT 5 cable, coaxial cable, optical fiber, etc). The signals through the various networks and the signals on the network link and through the communication interface, which carry the digital data to and from the computer system 1201 maybe implemented in baseband signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system can transmit and receive data, including program code, through the network(s) and, the network link and the communication interface. Moreover, the network link may provide a connection through a LAN to a mobile device such as a personal digital assistant (PDA) laptop computer, or cellular telephone.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method of correcting a target object in a computed tomographic (CT) image, the method comprising:
    obtaining a CT image of a patient;
    determining a size of the target object in the CT image; and
    correcting CT numbers of a portion of the CT image that corresponds to the target object, based on the determined size of the target object, wherein the correcting step includes correcting each CT number in the CT image that corresponds to the target object using the formula:

$$N=1-c^*\exp(-a^*D^{\wedge}b),$$

wherein a, b, and c are variables determined from non-linear regression, D is the determined size of the target object, and N is a reduction factor in CT number of the target object.

2. The method of claim 1, wherein the obtaining step comprises:
    performing a CT scan of the patient to obtain projection data; and
    performing reconstruction to obtain the CT image.

3. The method of claim 1, wherein the determining step comprises:
    segmenting the CT image to generate a segmented image;
    identifying the target object in the segmented image; and
    measuring the size of the identified target object.

4. The method of claim 3, wherein the measuring step comprises determining an effective radius of the target object.

5. The method of claim 3, wherein the measuring step comprises measuring one of a diameter, area, or volume of the target object.

6. The method of claim 1, wherein the correcting step further comprises:
    multiplying each CT number in the CT image that corresponds to the target object by 1/N.

7. A system for correcting a target object in a computed tomographic (CT) image, the system comprising:
    a CT scanner configured to perform a CT scan of a patient to obtain a CT image; and
    a processor configured to determine a size of the target object in the CT image, and to correct CT numbers of a portion of the CT image that corresponds to the target object, based on the determined size of the target object, wherein the processor is further configured to correct each CT number in the CT image that corresponds to the target object using the formula:

$$N=1-c^*\exp(-a^*D^{\wedge}b),$$

wherein a, b, and c are variables determined from non-linear regression, D is the determined size of the target object, and N is a reduction factor in CT number of the target object.

8. The system of claim 7, wherein the CT scanner is configured to perform the CT scan of the patient to obtain projection data, and to perform reconstruction to obtain the CT image.

9. The method of claim 7, wherein the processor is configured to determine the size of the target object by segmenting the CT image to generate a segmented image, identifying the target object in the segmented image, and measuring the size of the identified target object.

10. A non-transitory computer-readable medium that stores a computer program that, when executed by a computer, causes the computer to perform a method of correcting a target object in a computed tomographic (CT) image, the method comprising:
    obtaining a CT image of a patient;
    determining a size of the target object in the CT image; and
    correcting CT numbers of a portion of the CT image that corresponds to the target object, based on the determined size of the target object, wherein the correcting step includes correcting each CT number in the CT image that corresponds to the target object using the formula:

$$N=1-c^*\exp(-a^*D^{\wedge}b),$$

wherein a, b, and c are variables determined from non-linear regression, D is the determined size of the target object, and N is a reduction factor in CT number of the target object.

11. A method of determining a correction function for correcting computed tomographic (CT) numbers of a target object in a CT image obtained using a CT scanner, based on a geometric size of the target object, the method comprising:

performing a CT scan of a phantom having a plurality of inserts, each insert having a corresponding known physical density and a corresponding known geometric size, to generate CT image data for the phantom; and performing regression analysis on the CT image data to determine the correction function, the correction function relating attenuation in CT number to geometric size of the target object, wherein the step of performing regression analysis comprises determining a correction function of the form $N=1-c*\exp(-a*D^b)$, wherein a, b, and c are parameters determined from nonlinear regression, D is the geometric size of the target object, and N is a reduction factor in CT number of the target object.

12. The method of claim 11, wherein the geometric size of the target object is one of a diameter, area, and volume of the target object.

13. A system for determining a correction function for correcting computed tomographic (CT) numbers of a target object in a CT image obtained using a CT scanner, based on a geometric size of the target object, the system comprising:

the CT scanner configured to perform a CT scan of a phantom having a plurality of inserts, each insert having a corresponding known physical density and a corresponding known geometric size, to generate CT image data for the phantom; and a processor configured to perform regression analysis on the CT image data to determine the correction function, the correction function relating attenuation in CT number to geometric size of the target object, wherein the processor is configured to perform regression analysis by determining a correction function of the form $N=1-c*\exp(-a*D^b)$, wherein a, b, and c are parameters determined from nonlinear regression, D is the geometric size of the target object, and N is a reduction factor in CT number of the target object.

14. A non-transitory computer-readable medium that stores a computer program that, when executed by a computer, causes the computer to perform a method of determining a correction function for correcting computed tomographic (CT) numbers of a target object in a CT image obtained using a CT scanner, based on a geometric size of the target object, the method comprising:

performing a CT scan of a phantom having a plurality of inserts, each insert having a corresponding known physical density and a corresponding known geometric size, to generate CT image data for the phantom; and performing regression analysis on the CT image data to determine the correction function, the correction function relating attenuation in CT number to geometric size of the target object, wherein the step of performing regression analysis comprises determining a correction function of the form $N=1-c*\exp(-a*D^b)$, wherein a, b, and c are parameters determined from nonlinear regression, D is the geometric size of the target object, and N is a reduction factor in CT number of the target object.

* * * * *